United States Patent [19]

Cushman et al.

[11] Patent Number: 4,936,138
[45] Date of Patent: Jun. 26, 1990

[54] METHOD AND APPARATUS FOR TIRE INSPECTION

[75] Inventors: Charles R. Cushman; Loren J. Dikeman, both of Montrose, Colo.

[73] Assignee: Oliver Rubber Company, Oakland, Calif.

[21] Appl. No.: 364,997

[22] Filed: Jun. 9, 1989

Related U.S. Application Data

[63] Continuation-in-part of Ser. No. 244,818, Sep. 14, 1988, abandoned.

[51] Int. Cl.$^5$ ............................................. G01N 29/04
[52] U.S. Cl. ......................................... 73/146; 73/618
[58] Field of Search ................. 73/582, 588, 598, 599, 73/600, 618, 619, 634, 637, 146, 609

[56] References Cited

U.S. PATENT DOCUMENTS

| | | | |
|---|---|---|---|
| 3,336,794 | 8/1967 | Wysoczanski | 73/67.5 |
| 3,961,523 | 6/1976 | Cornforth | 73/67.8 |
| 4,275,589 | 6/1981 | Dugger et al. | 73/600 |

FOREIGN PATENT DOCUMENTS 1479594  9/1973  United Kingdom .

*Primary Examiner*—Michael J. Tokar
*Assistant Examiner*—Mark A. Spector
*Attorney, Agent, or Firm*—Owen, Wickersham & Erickson

[57] ABSTRACT

An apparatus for inspecting a tire for structural defects as the tire is rotated on a stand comprises a movable transducer transmitter for directing a plurality of successive collimated bursts of ultrasonic energy against the tire surface, said bursts passing through the tire and forming inspection areas having the same diameter and overlapping each other as the tire is rotated during an inspection cycle. A movable receiver transducer located on the other side of the tire from the transmitter is constantly positioned to receive the collimated ultrasonic energy that passes through each inspection area. Coordination control elements are provided for moving the transmitter transducer and the receiver transducer from one side of the tire to the other generally parallel to its axis of rotation while successive ultrasonic bursts are directed through the tire as it rotates during each inspection test and while maintaining substantially the same distance between the transducers for each burst. The strength of the energy received by the receiver transducer is evaluated for each burst when the evaluation indicates that a defect is present, a visual indicator is triggered to identify the location of the structural defect in the tire being inspected.

40 Claims, 15 Drawing Sheets

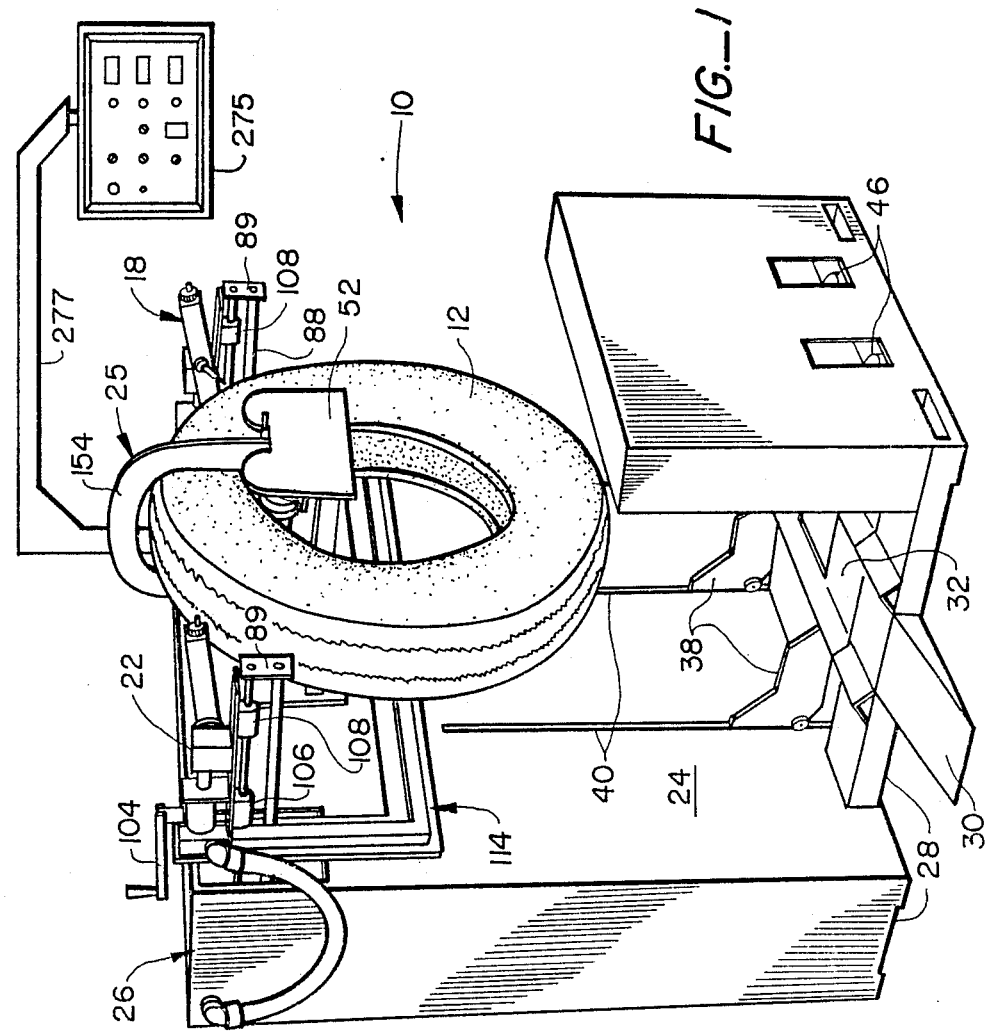
FIG.—1

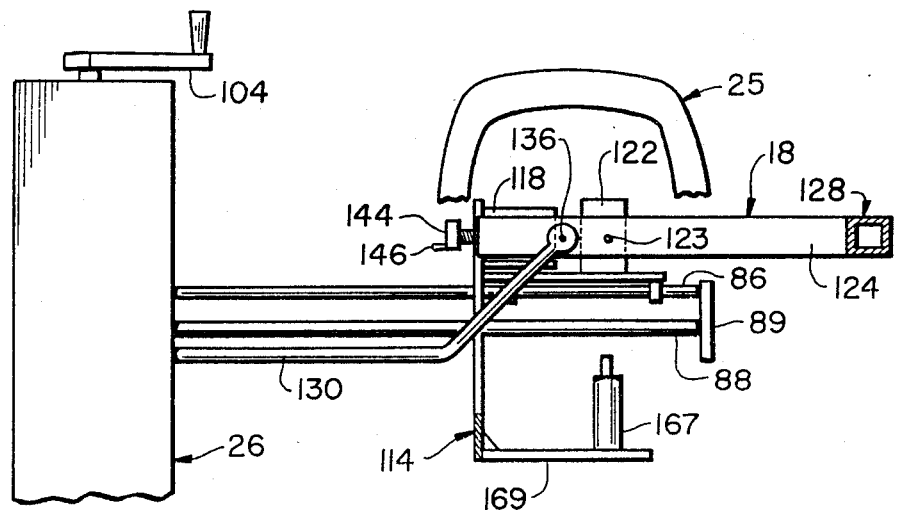
FIG._3C
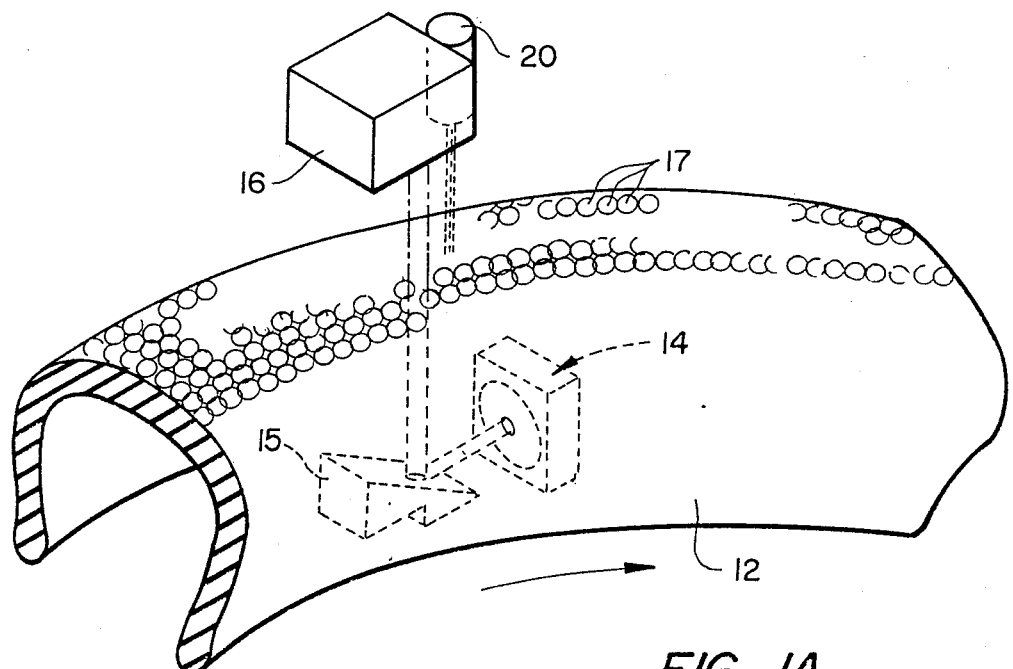
FIG._1A

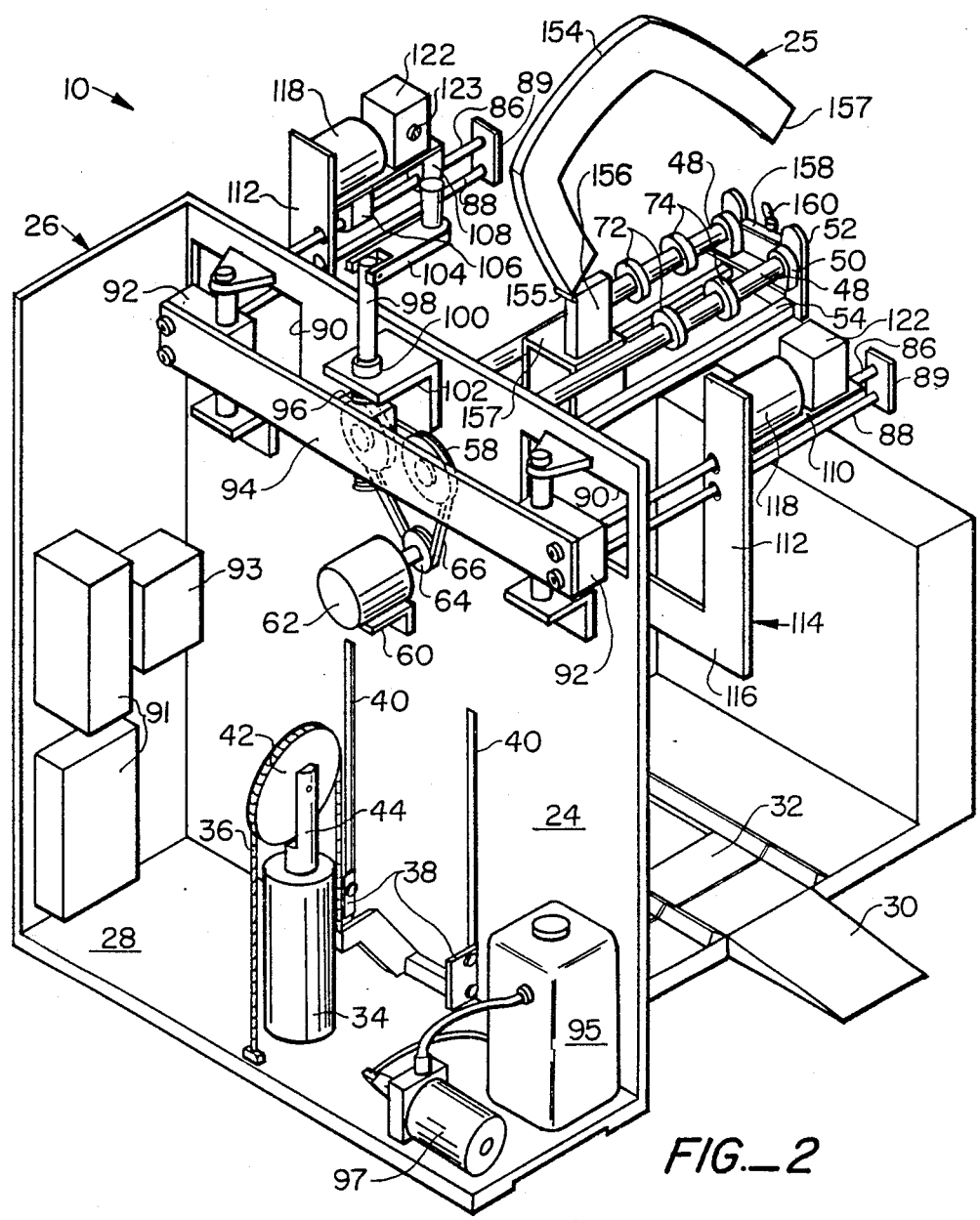
FIG._2

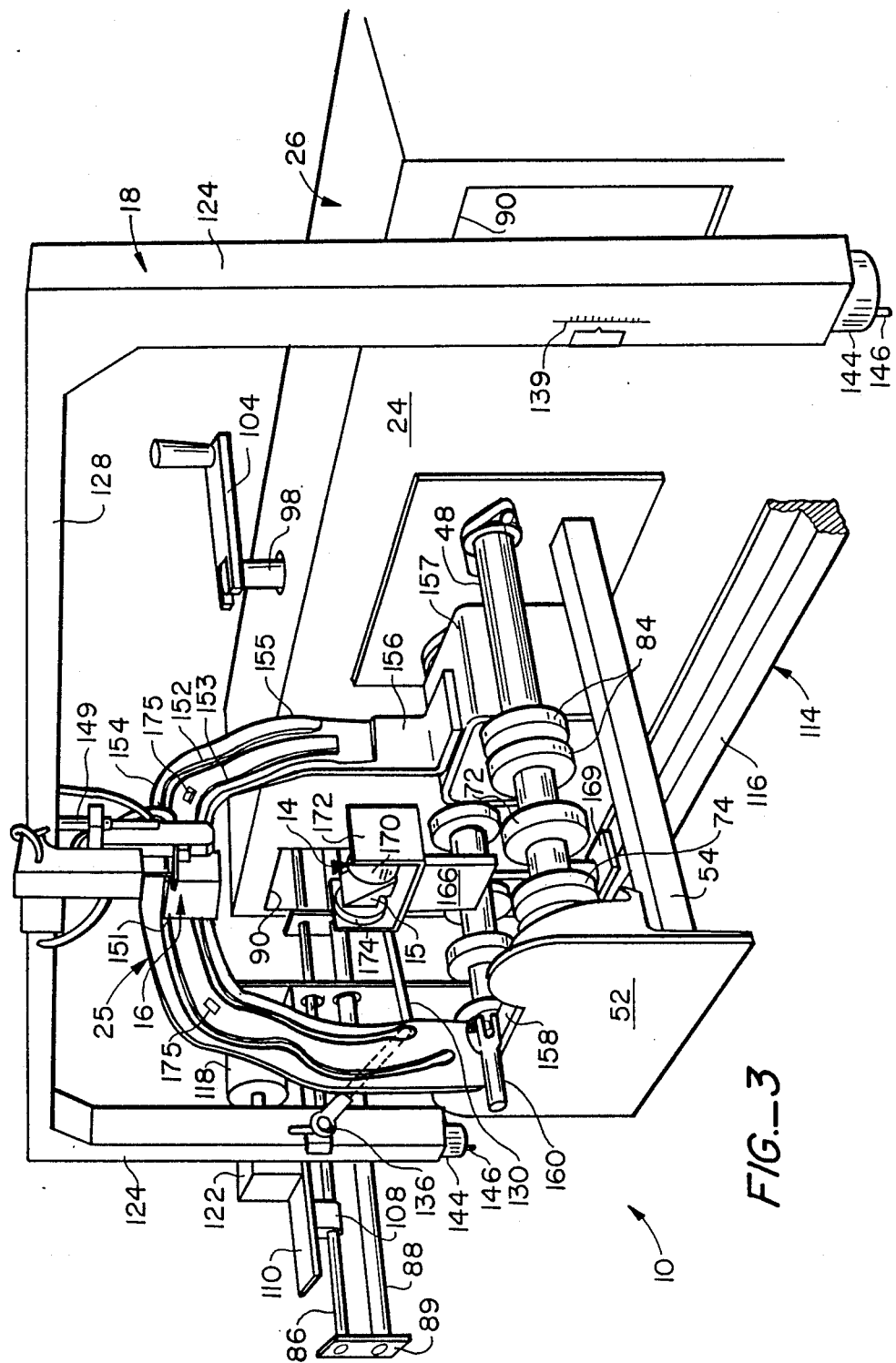
FIG._3

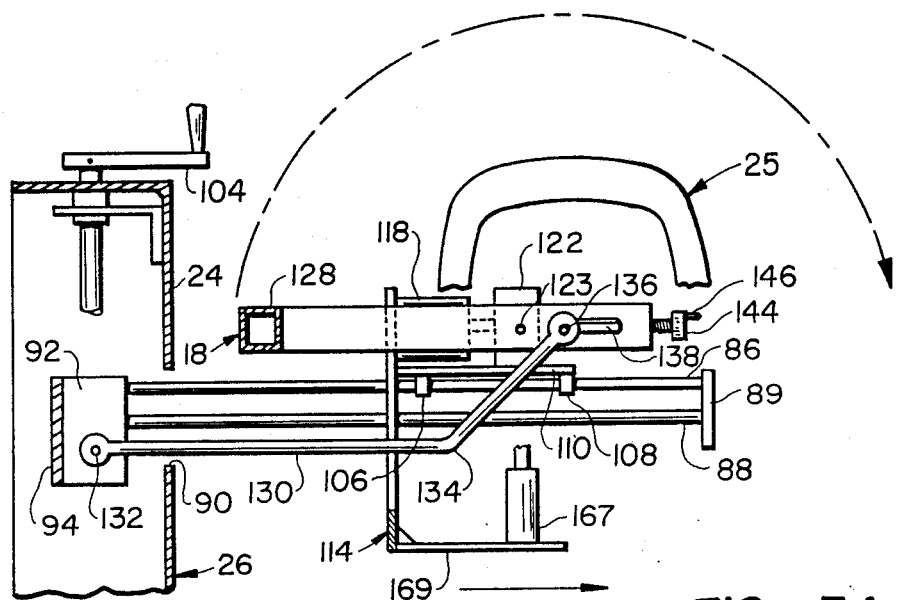
FIG._3A
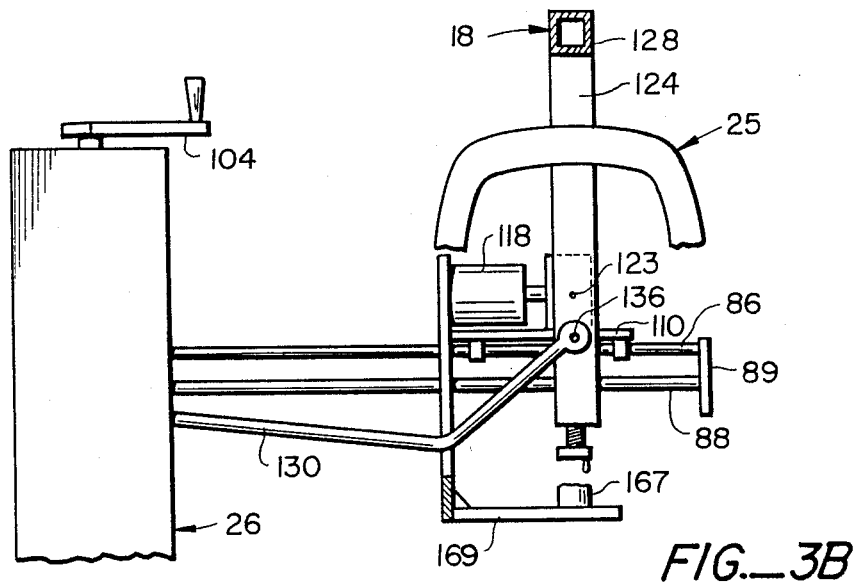
FIG._3B

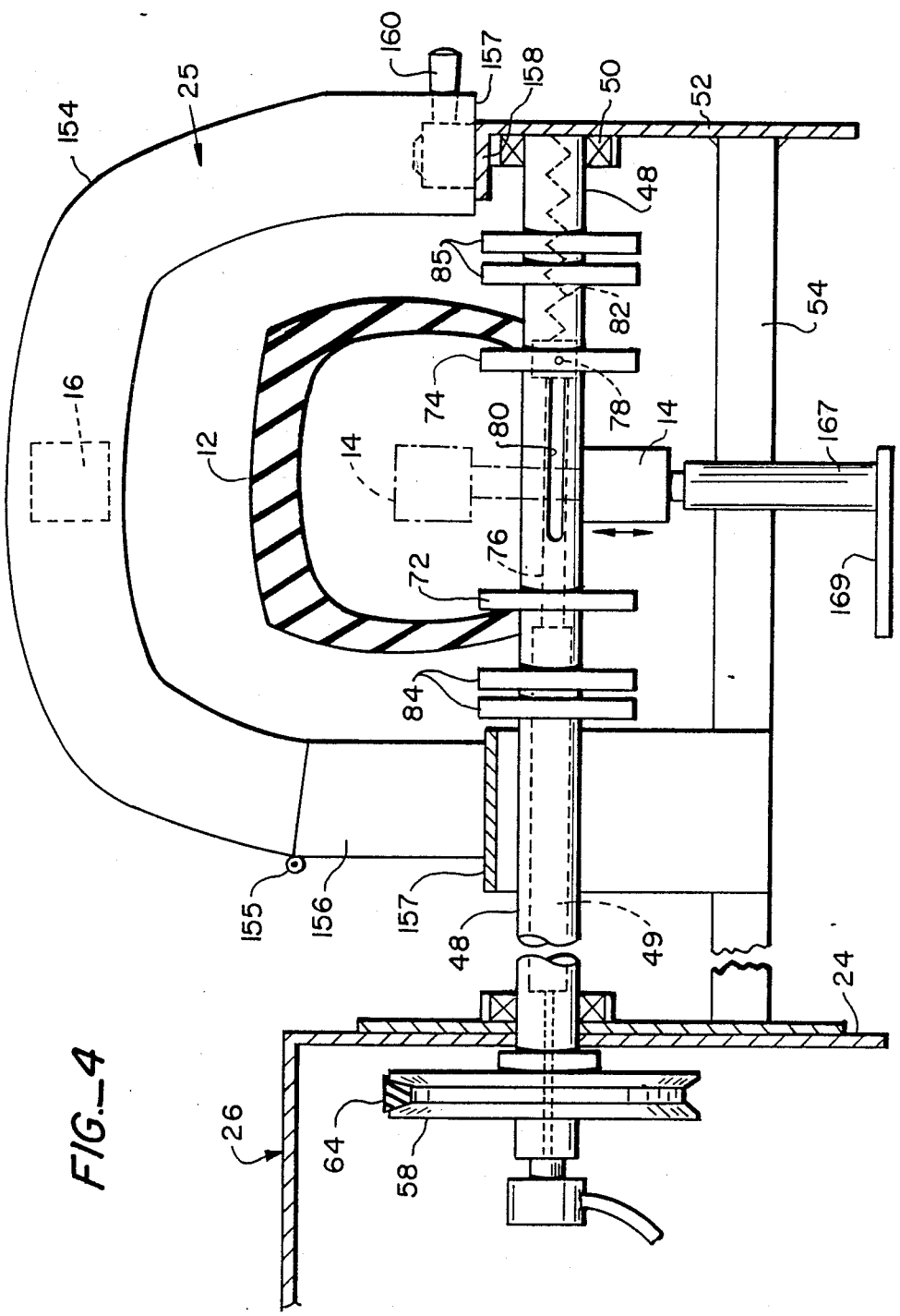
FIG._4

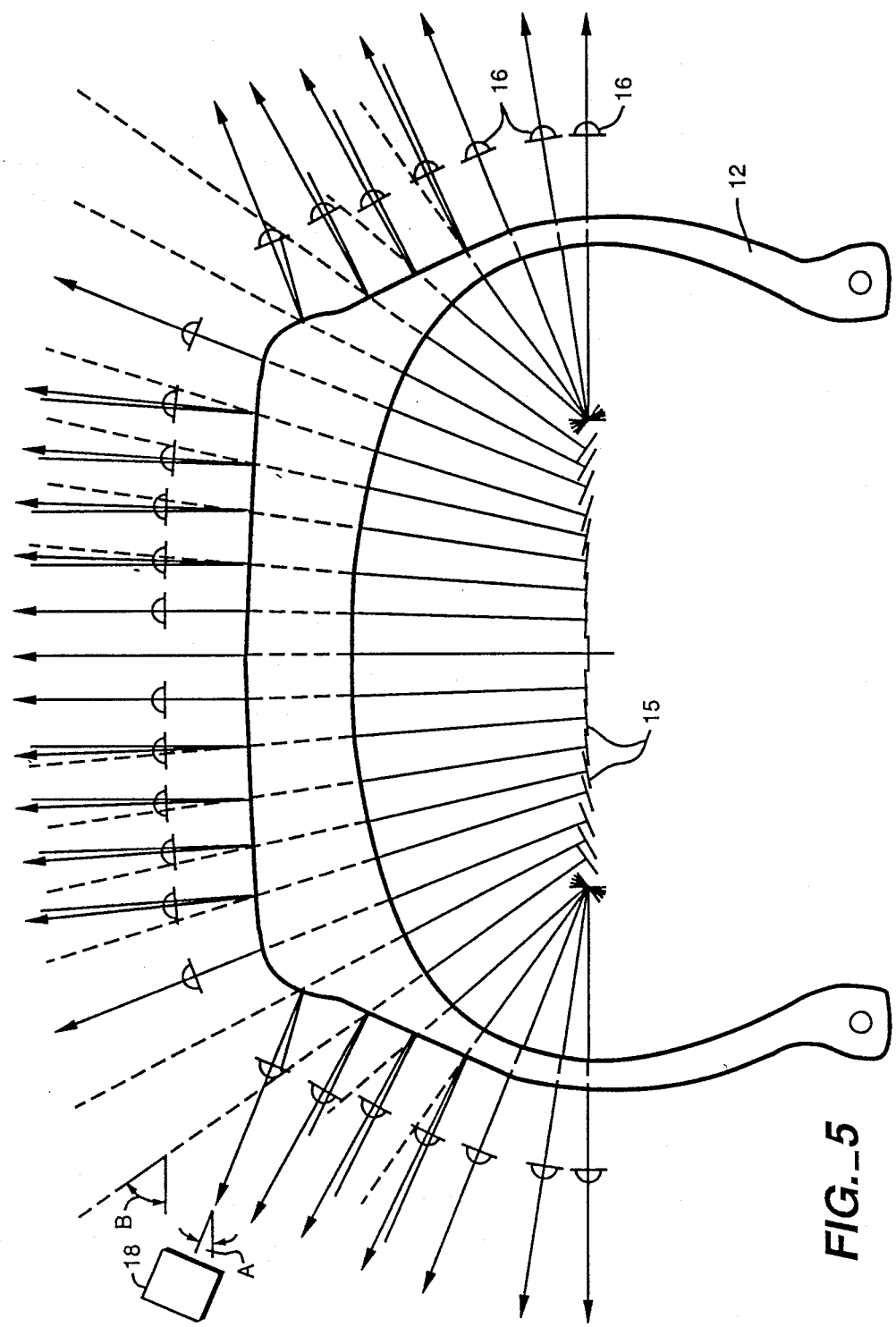
FIG._5

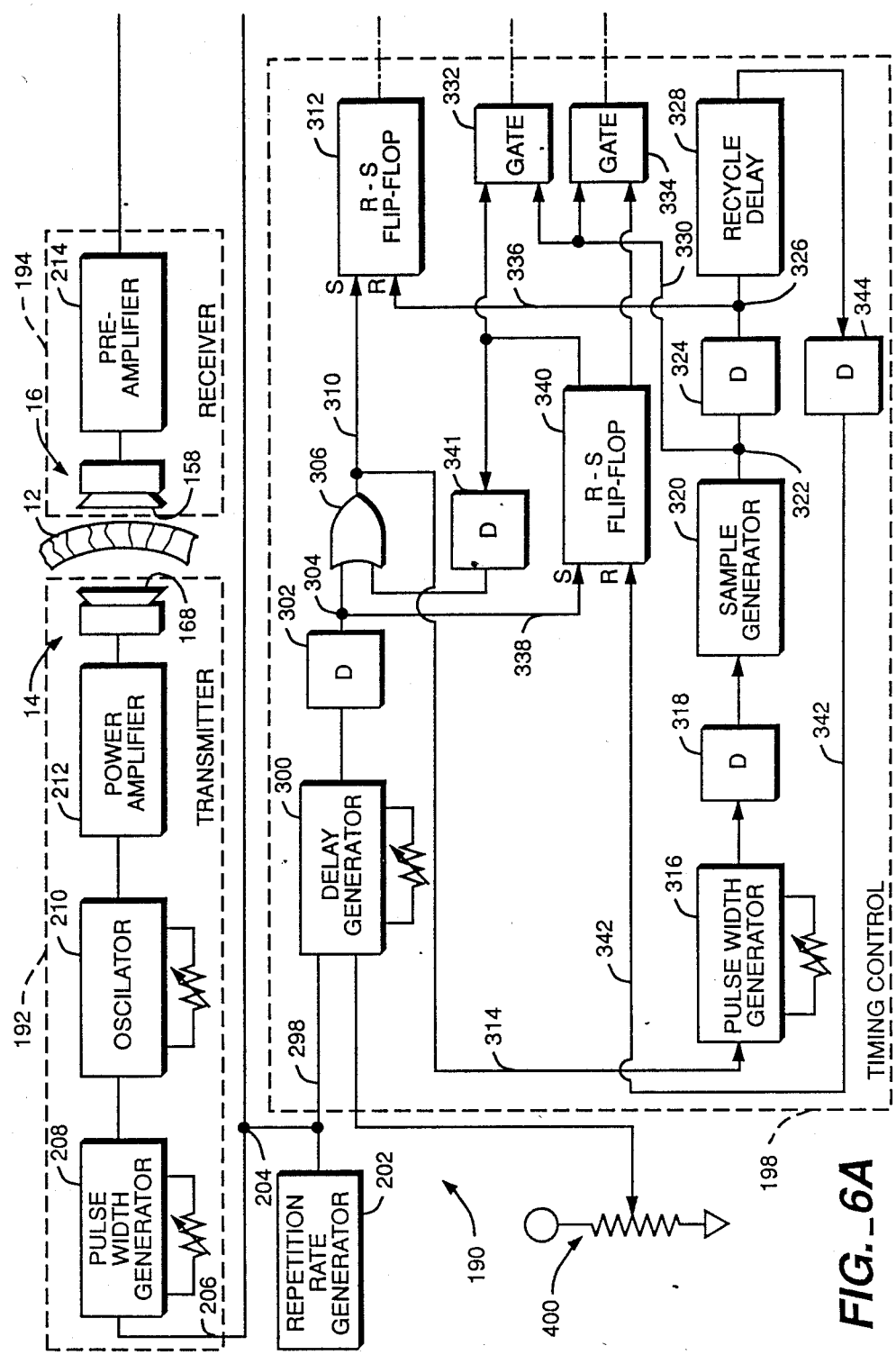
FIG._6A

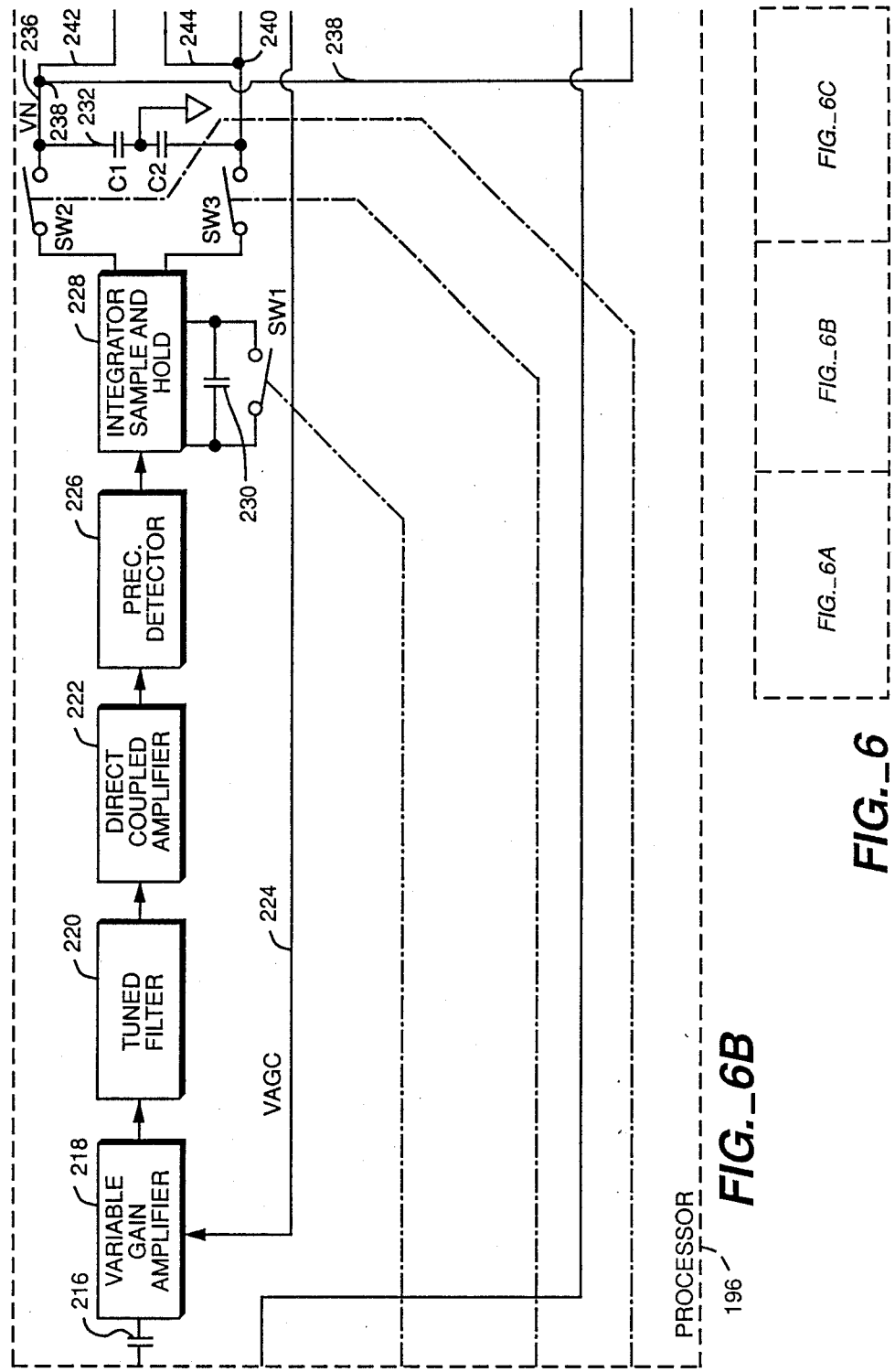

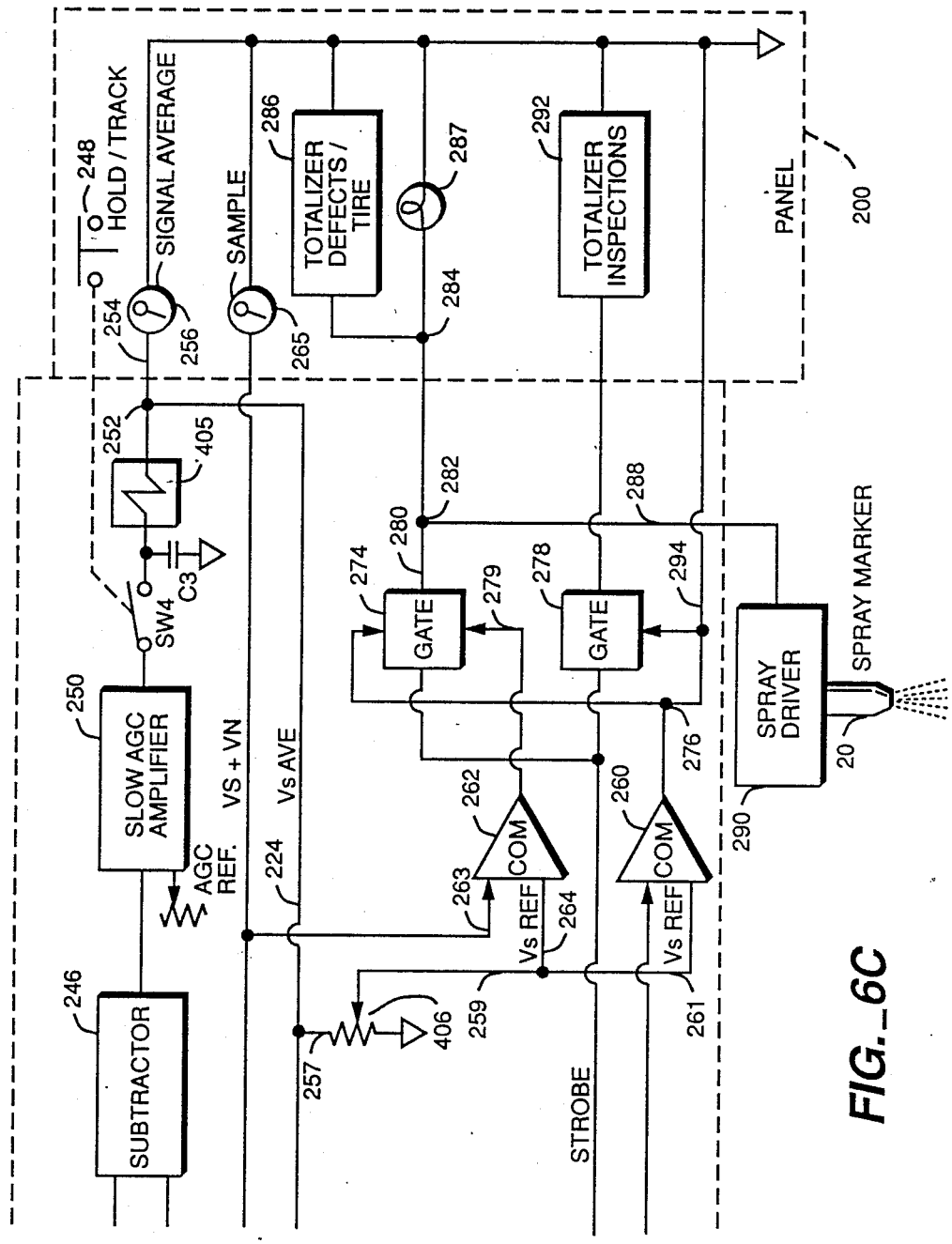
FIG._6C

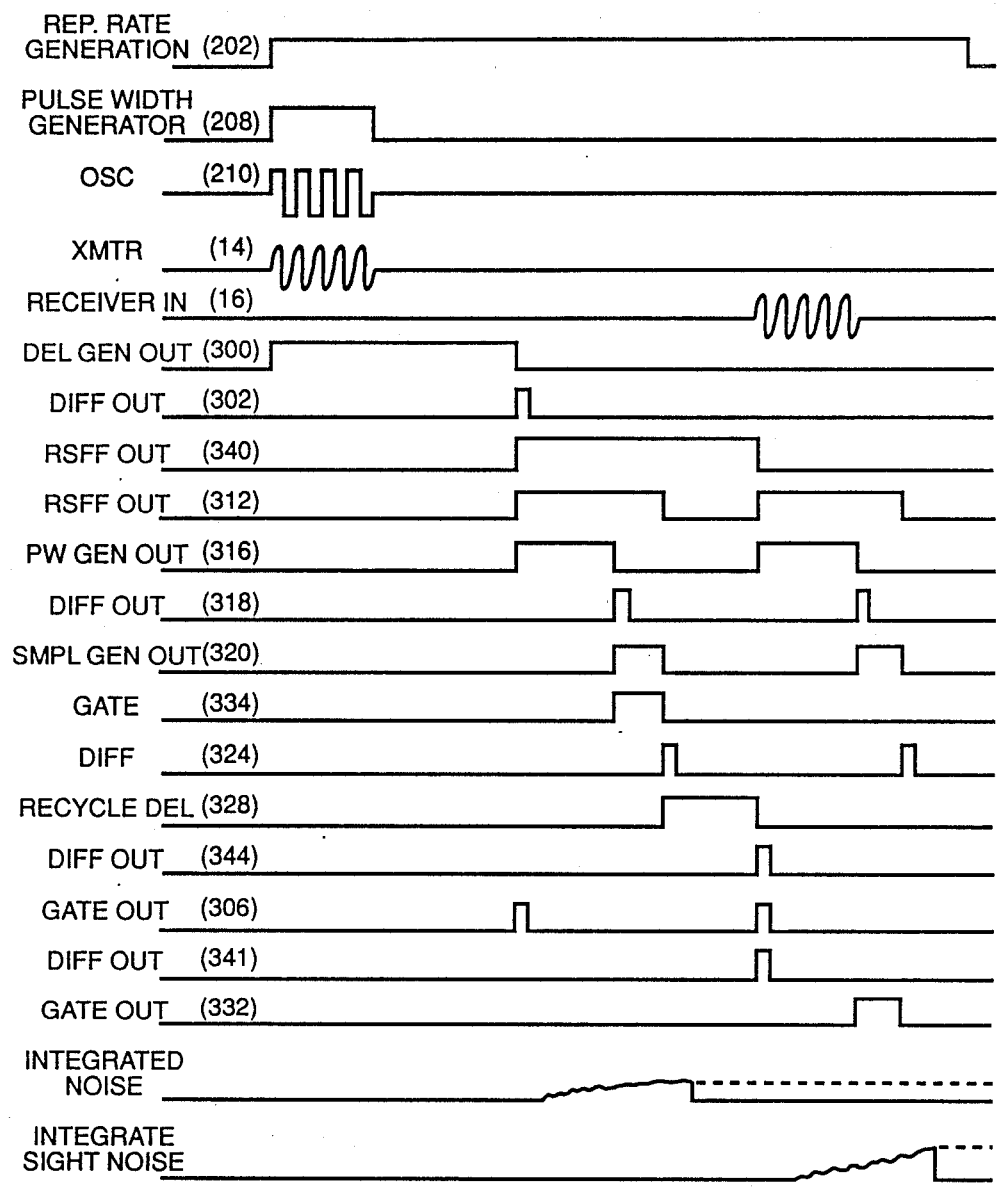
FIG._7

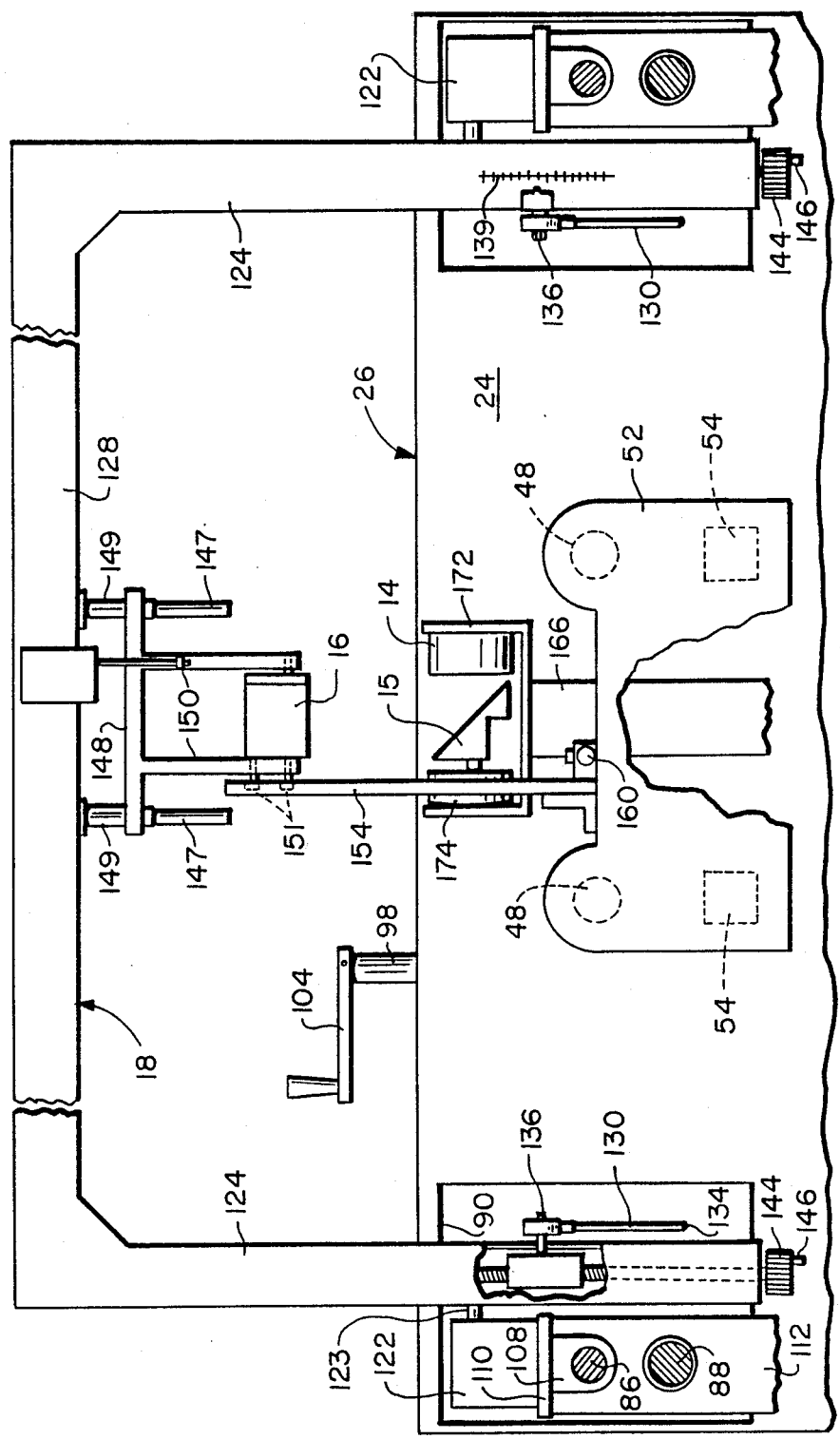
FIG._8A

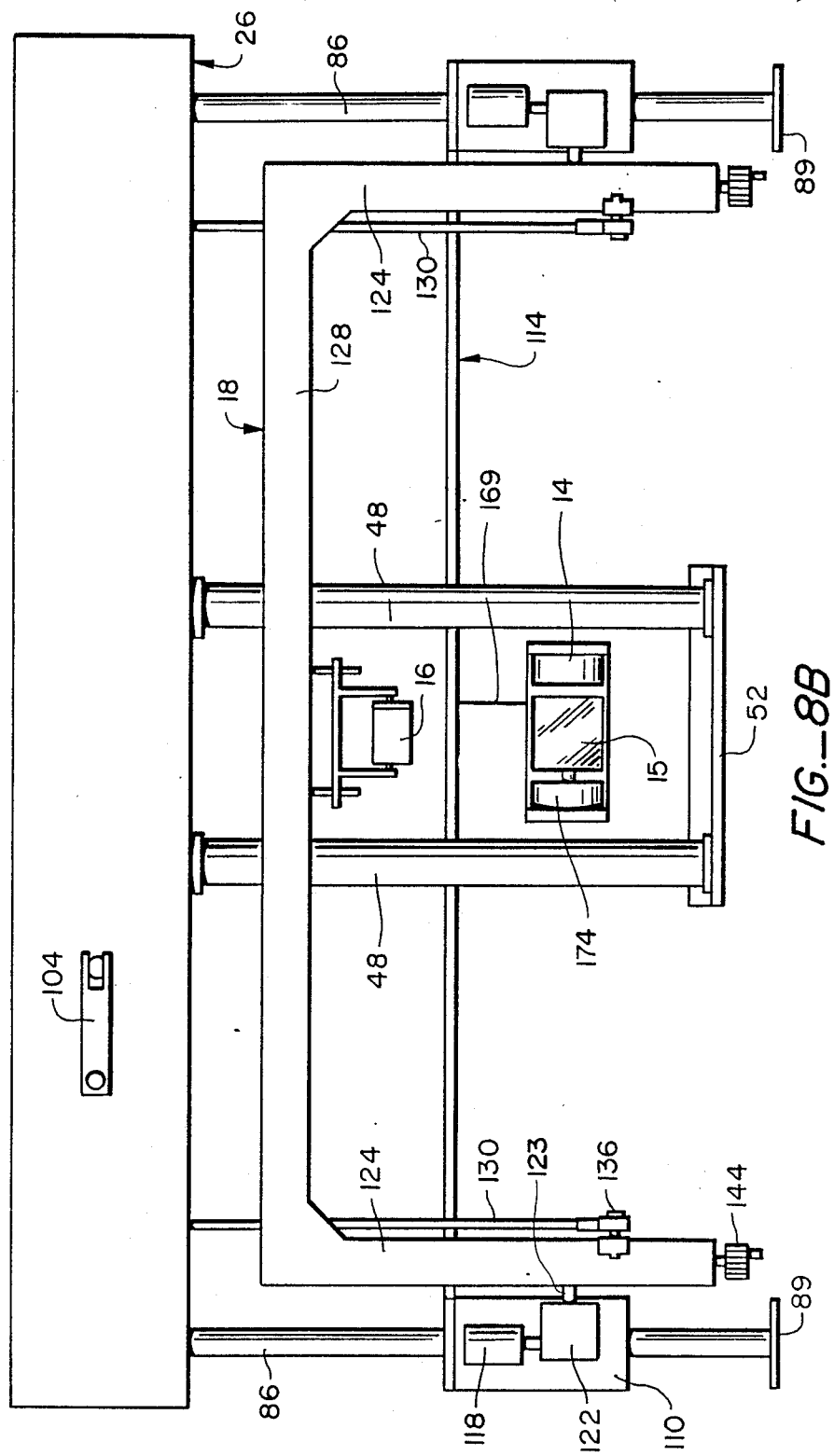

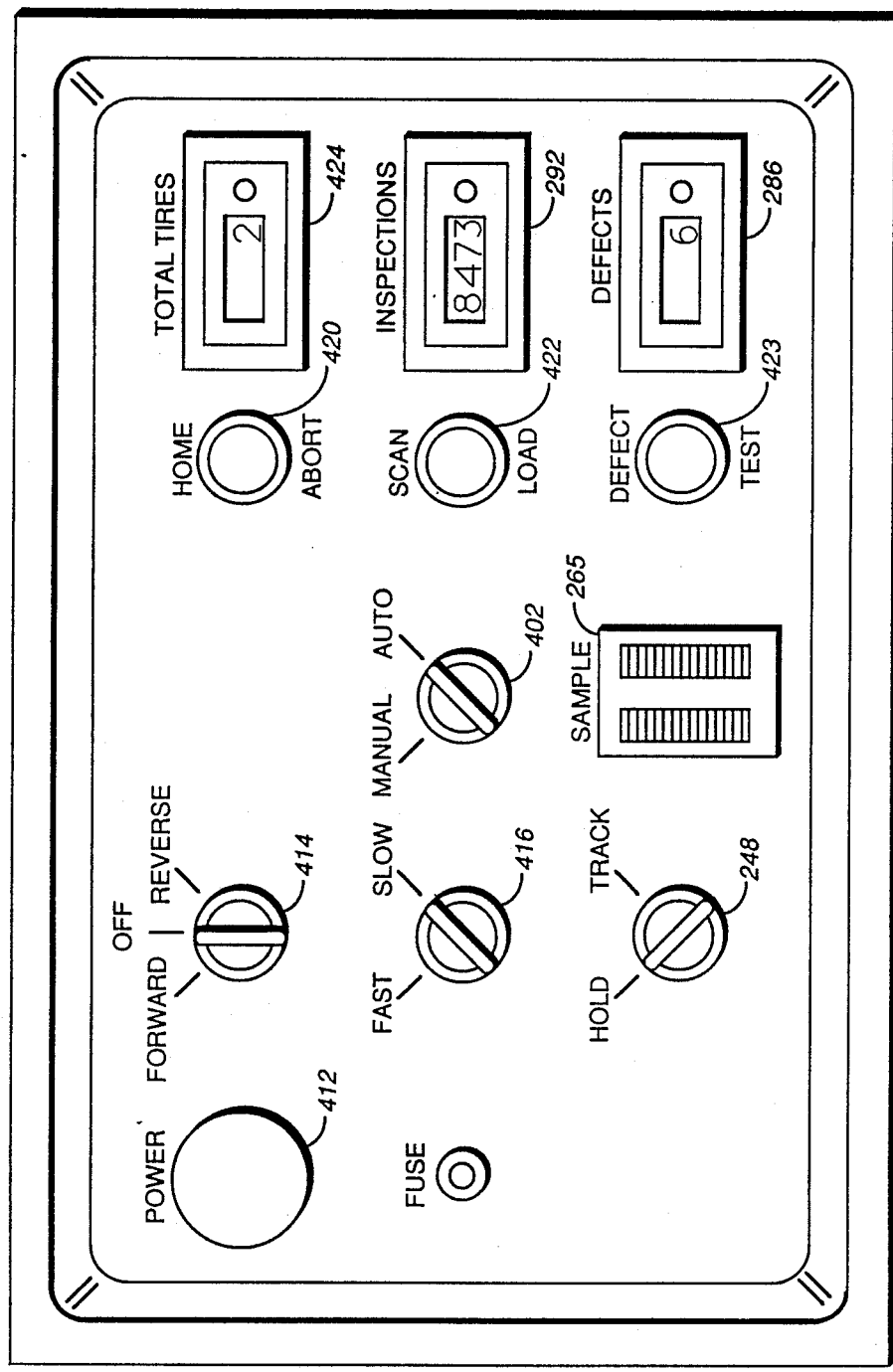
FIG._9

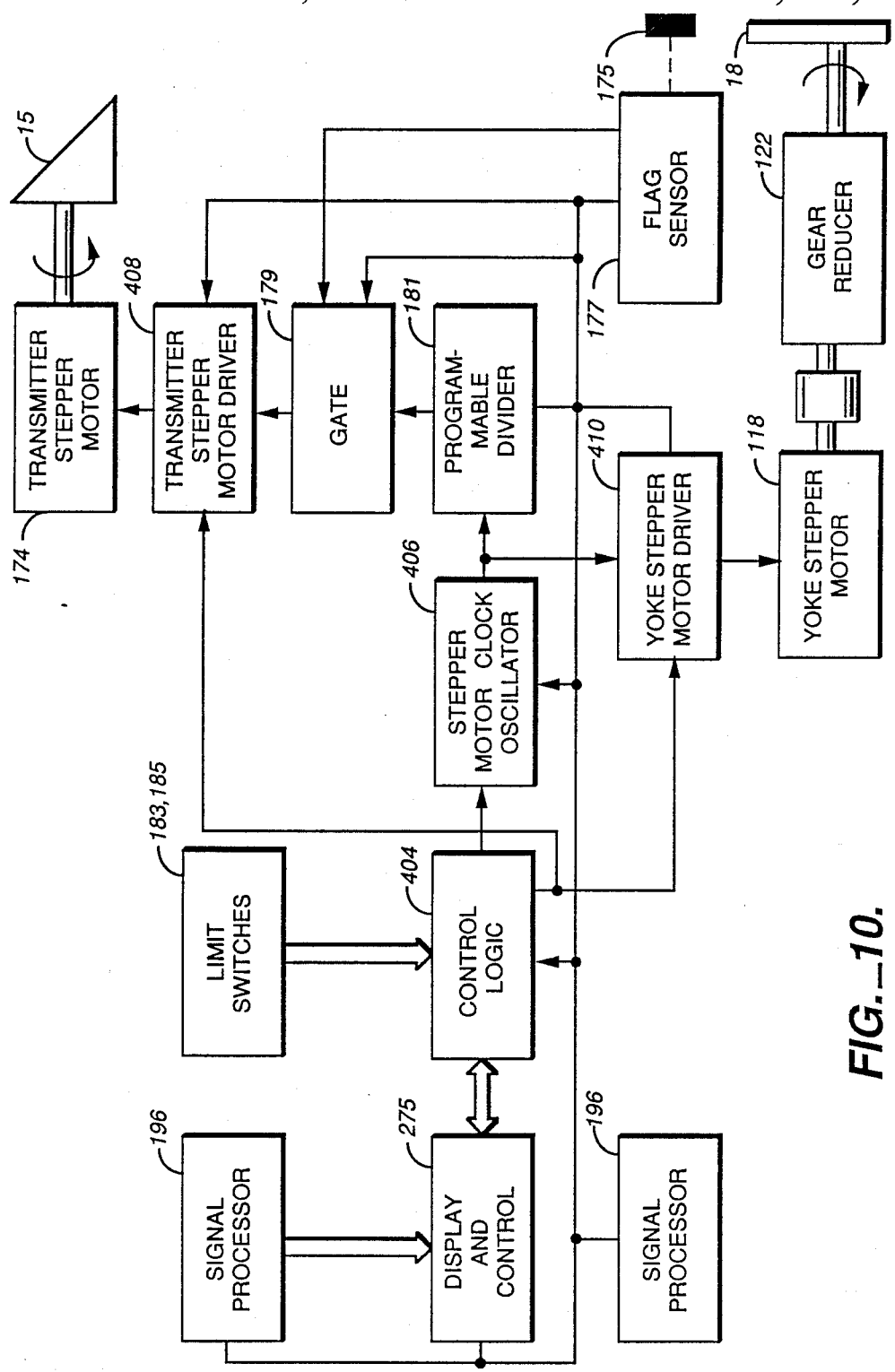
FIG._10.

METHOD AND APPARATUS FOR TIRE INSPECTION

This application is a continuation-in-part of application Ser. No. 07/244,818, now abandoned, filed Sept. 14, 1988.

This invention relates to methods and apparatus for the non-destructive inspection of rubber tires, and more particularly it relates to an improved system wherein a multiplicity of discrete pulses of ultrasonic energy are directed through a tire to detect hidden structural defects.

BACKGROUND OF THE INVENTION

In tire retreading operations, it is highly desirable, if not essential to make a thorough inspection of a tire casing before subjecting it to the retreading process. If the tire casing is retreaded with some latent defect, it must later be discarded when the defect is discovered and, until discovered, the defect may constitute a serious safety hazard.

Heretofore, efforts have been made to provide adequate non-destructive tire inspection apparatus utilizing vibration techniques, X-rays or ultrasonic energy as the media for analyzing the tire structure. Recent examples of a tire inspection apparatus utilizing ultrasonic energy are found in U.S. Pat. Nos. 4,266,428, 4,275,589 and 4,365,514. However, such prior inspection systems and apparatus have not provided a level of performance, i.e. speed, accuracy and reliability, that has been sufficient to gain wide acceptance in the tire recapping industry. In prior tire inspection apparatus, as described in the aforementioned patents, the ultrasonic energy is provided in relatively long bursts inside an inflated tire being inspected to acoustically illuminate the entire inside surface of the tire. As the tire was rotated on the apparatus, the acoustic energy passing through the tire was sensed by plural acoustic receiving transducers arranged in a fixed preset array about the outer tire walls. Variations in received signals by the receiving transducers of the array were presumed to provide a basis for detecting flaws or leaks in the tire carcass. However, in this prior art device certain difficulties arose such as the leakage of relatively high levels of acoustic energy within the inflated tire which often interfered with the reception of clear signals by the arranged receiving transducers. Thus, the accuracy and dependability of the inspection system with regard to the consistent identification of the anomalies was often unacceptable and in need of improvement.

To overcome the deficiencies of prior tire inspection systems, the present system was conceived utilizing high frequency acoustics in a through transmission arrangement comprising the combination of a transmitting pulse generator, a transmitting transducer for producing collimated bursts of ultrasonic energy, a separate receiving transducer, so placed to receive the acoustic energy transmitted through the material, an acoustic coupling medium on both sides of the material and amplifiers, processors and indicators or displays. However, the inspection of tires by such acoustic means presented particular problems due to the inherent factors such as: (1) the requirement that the coupling medium between transducers and the tire material must be air; (2) the tire has an irregular shape; (3) the tire inspection apparatus for tires is commonly located in areas where ambient noise levels are high which affects the evaluation of test signal data; and (4) the acoustic transmitter and receiver must be coordinated to move in concert to assure that the transmitted collimated energy is properly received for each burst.

Although it is more practical to use air as a coupling medium for tire inspection, significant problems exist with its use, such as: (1) air coupled transmitting transducers are of fairly limited output intensity; (2) a large acoustic impedance mismatch exists between air and any solid material being inspected; (3) a large refraction of the acoustic energy occurs at the entry and exit surface when the acoustic "beam" is not normal to these surfaces. (The index of refraction between air and rubber is approximately 5); and (4) a significant ambient noise level exists in most industrial environments in which a system is operating.

With regard to the tire shape, the refraction effect in an air medium becomes a serious problem because: (1) the inner and outer surfaces are not coaxial; (2) the outer surface is fairly flat on the running surface and cylindrical on the side walls; and (3) the inner surface may have a large degree of eccentricity.

A general object of this invention is therefore to provide an improved tire inspection system that overcomes the aforesaid problems and will: (1) utilize a highly directional transmitting transducer to efficiently "illuminate" an area on the inner surface of the tire and be maintained near normal to that area; (2) utilize a highly directional receiving transducer that is relatively insensitive to ambient noise, and maintain it in a position that is near normal to the outer surface of the tire; (3) control the relative positions of the transmitter and receiver transducers so that the receiver is always aligned in the area of the exiting refracted acoustic energy; (4) minimize the effect of varying ambient noise on the automatic gain controls within the signal processor.

Other objects of this invention are to provide a tire inspection apparatus that: (1) is relatively easy to operate by persons having an ordinary level of skill; (2) is highly accurate in detecting tire defects: (3) provides a visual mark at the location on the tire for each defect detected; (4) provides a displayed readout of the number of inspection pulses and the number of defects detected; and (5) is reliable and relatively easy to service and maintain.

SUMMARY OF THE INVENTION

In accordance with the principles of the present invention a tire inspection apparatus is provided which, in broad terms, comprises a means for supporting an uninflated tire casing while rotating it at a constant, controllable rate as the tire tread and sidewall areas are covered by a plurality of sequential bursts of collimated ultrasonic energy Within the tire casing is an ultrasonic transmitter transducer which is movable by a control mechanism to transverse across the width of the tire and also rotate angularly as it intermittently emits pulses of ultrasonic energy directed at the inside tire surface and through the tire. Spaced from the outer surface of the tire is an ultrasonic energy receiver that is also moveable to receive each energy pulse from the transmitter transducer which passes through the tire. The ultrasonic transmitter and receiver transducers are coordinated together as they move so that the receiver unit is always in near perfect alignment to receive the collimated pulse of energy from the transmitter unit. Thus, in a typical tire inspection cycle, as the tire is rotating, the transmitter unit is moved transversely across the width of the tire while its collimated beam is swept angularly by a stepped rotational drive. The transmitter transducer produces rapid collimated pulses of energy which are received by the pulse receiver transducer outside the tire, after the collimated energy has passed through a small circular area on the tire. After each transmitted pulse, during an inspection cycle, the received energy, converted to an integrated electrical signal voltage, is furnished to a comparator in an electrical circuit wherein a change of signal from a derived average, due to an anomaly in the tire such as a delamination is detected. The resulting comparator output is fed through a gate to a sprayhead driver mounted on the receiver transducer which operates- to mark the tire immediately in the area of the detected defect. The electrical circuit provides a two-pass arrangement for separately measuring a noise only and a noise plus signal value. From these values, a signal only value is obtained for use in providing AGC feedback that eliminates the effects of any large extraneous test signal variations. Also, the measurement of noise during every inspection cycle causes the system to automatically negate inspections when ambient noise becomes excessive.

In the embodiment disclosed, the transmitter transducer utilizes a rotatable mirror or deflector to facilitate the transmission of collimated ultrasonic energy pulses. The transmitter transducer is mounted within the tire and its transverse movement during an inspection cycle is controlled by a master stepper motor that drives a rotatable yoke which is also transversely moved by a pair of adjustable stroke crank arms. The receiver transducer is mounted on the yoke and its movement during an inspection cycle is also controlled by a cam plate that extends around the outside of the tire. As the transmitter transducer transverses from one side of the tire to the other it progressively rotates by an amount necessary to constantly direct collimated bursts of ultrasonic energy at substantially a right angle to the inner tire surface for each burst. Simultaneously, the receiver transducer is constantly controlled by the guiding cam plate so as to be substantially normal to the tire's surface in order to receive most efficiently the collimated ultrasonic energy which passed through the tire from the transmitter with each burst. As the tire rotates, its critical area becomes completely covered by overlapping circular inspection areas. For each inspection area a comparative check is electronically made between received signals and a derived base value to determine signal fluctuations that indicate when flaws or anomalies in the tire structure are present within that area. Each tire inspection requires two to three minutes of actual inspection time and any detected flaws in the tire are marked automatically.

Other objects, advantages and features of the invention will become apparent from the following detailed description of one embodiment thereof, presented in conjunction with the accompanying drawings.

BRIEF DESCRIPTION OF THE DRAWING

FIG. 1 is a frontal view in perspective of a tire inspection apparatus embodying principles of the present invention.

FIG. 1A is a fragmentary diagrammatic view indicating the formation of multiple inspection areas formed by successive bursts of ultrasonic energy.

FIG. 2 is a rear fragmentary view in perspective of the apparatus of FIG. 1, with side and back panels removed to show internal components.

FIG. 3 is an enlarged frontal view in perspective of a fragmentary upper portion of the apparatus of FIGS. 1 and 2, showing a mechanism for manipulating transmitter and receiver transducer elements in accordance with the invention. Elements of the yoke assembly are not shown.

FIGS. 3A-3C are a series of diagrammatic views of the apparatus of FIG. 1, showing movement of the yoke assembly during an inspection cycle.

FIG. 4 is a fragmentary diagrammatic view in section of the apparatus of FIG. 1, showing a tire in cross section and spacer elements for spreading the tire beads.

FIG. 5 is a diagrammatic view of a typical tire in cross-section showing a series of positions for transducer and receiver elements of the inspection apparatus during a typical inspection cycle according to the invention.

FIGS. 6A and 6B comprise a block and circuit diagram of one portion of the apparatus illustrating the circuitry for processing the data developed during an inspection cycle according the invention.

FIG. 7 is a timing diagram illustrating the operation of certain components of the circuit FIG. 6.

FIG. 8A is a fragmentary frontal view of the apparatus of FIG. 1 showing the yoke in a vertical, intermediate position.

FIG. 8B is a fragmentary top view of the apparatus of FIG. 1, showing the yoke in a horizontal, starting position.

FIG. 9 is an enlarged view of the front side of the control and display unit for the apparatus of FIG. 1.

FIG. 10 is a block diagram showing the control logic and stepper motor drive system for the tire inspection apparatus of FIG. 1.

DETAILED DESCRIPTION OF EMBODIMENT

With reference to the drawing, FIG. 1 shows a nondestructive tire inspection apparatus 10 embodying principles of the present invention, shown with a tire 12 supported in its normal position during an inspection cycle. In broad terms, the apparatus utilizes a single ultrasonic transmitter transducer means 14 situated within the tire (see FIG. 1A) which generates collimated bursts or pulses of acoustic energy directed at the inside tire surface and adapted to be received by a moveable receiver transducer means 16 located outside the tire. The transmitter transducer means includes a rotatable mirror 15 whose orientation and movement is controlled and coordinated with movement of the receiver transducer means in accordance with the invention. Each burst of collimated energy passes through the tire wall at a relatively small area 17 and can be accurately evaluated to detect tire anomalies or defects. The transmitter transducer means is controlled in its movement so as to scan the tire from sidewall to sidewall with time-spaced acoustic pulses as the tire is rotated. Thus, as shown in FIG. 1A, during a complete inspection cycle, the tire 12 is covered by a multiplicity of overlapping circular areas 17 arranged in a spiral pattern across the tire, each area representing a collimated pulse of acoustic energy that passes through the tire. When a defect is detected for one such area, a marker device 20 is activated after a preset delay to indicate the exact defect location on the tire. The receiver transducer means 16 is mounted on a moveable yoke 18 assembly that extends above the tire and has an axis of rotation generally perpendicular to the tire's axis of rotation. Associated with the yoke is a coordinating means 22 including a cam guide means 25 which assures that, as the transmitting transducer 14 scans the tire from inside, the receiver transducer 16 outside the tire is constantly aligned to receive the collimated acoustic energy that passes through the tire and is emitted from the outer surface of the tire. The movement of the transmitting transducer is also controlled to assure that each pulse of the collimated acoustic energy strikes the inside of the tire at substantially a right angle to the tire surface. The coordinating means simultaneously controls the movement of the receiver transducer so as to assure that it is positioned to receive the collimated acoustic energy of each pulse which leaves the outer surface of the tire at generally a right angle. A detailed description of the coordinating means will be set forth below with reference to FIGS. 3 and 3A–3C.

For each pulse of collimated energy, the receiver transducer 16 registers a value that is compared with a preset value established within a defect detection circuit 23, shown in FIG. 6. A variation of the received signal with the preset signal value produces an error signal indicating a defect within the tire structure such as a layer delamination or the like. As the inspection cycle proceeds, each error signal generated actuates the marking device 20 which operates to project a marking substance, such as an ink or paint, onto the outer surface of the tire precisely in the area where the pulse was directed when the error signal was detected. Thus, as a tire undergoes an inspection cycle, the areas of defects or discontinuities are automatically marked wherever they occur in each circular area produced by a test pulse.

Describing now the apparatus 10 in greater detail, its major mechanical components are supported on a vertical plate 24 which forms one wall of an enclosure 26 supported on a base 28 attached to a lift platform 32 outside the enclosure. The latter has ramp members 30 extending from its opposite sides so that the tire 12 to be inspected can be easily rolled up a ramp member and onto the lift platform.

As shown in FIG. 2, the lift platform 32 is controlled by a hydraulic actuator 34 having conventional operating controls and supported on a portion of the base member extending rearwardly from the vertical plate. A lift linkage is provided which is comprised of a roller chain 36 anchored at one end to the base member 28 and attached at the other end to a pair of arms 38 extending from the lift platform through slots 40 in the vertical plate 24. The chain 36 extends over an idler sprocket 42 which is attached to a cylinder rod 44 of the actuator 34. A conventional foot control 46 (FIG. 1) may be provided to control the actuator, so that as soon as a tire is moved onto the lift platform, it can be quickly and easily raised for mounting on the testing apparatus.

In its testing position, the tire is supported on two horizontal, spaced apart parallel roller shafts 48. These shafts are supported at their outer ends in bearing blocks 50 that are mounted on a vertical end plate 52 attached to two parallel supports 54 which are cantilevered outwardly from the vertical wall plate 24. The inner ends of the two roller shafts 48 extend through the vertical wall plate and the inner end of each shaft 48 is fixed to a sheave 58, as shown in FIG. 2. Mounted on a support 60 which is attached to the inside surface of the vertical plate 24 is an electrical drive motor 62 (e.g. ¼ H.P.) having a pulley wheel 64 on its input shaft. The pulley wheel and the sheaves 58 are connected by a continuous V-belt 66, so that when the motor is activated, the tire support roller shafts 48 will rotate at a constant R.P.M. In order to provide a reasonably rapid but efficient inspection period for each tire of around two to three minutes, the roller shafts are rotated at a speed necessary to provide a tire rotational surface speed of approximately 280 ft./min.

When a tire is ready for an inspection cycle it is raised by the lift platform and placed on the two roller shafts 48 which contact the tire beads at spaced apart locations. Prior to initiating the inspection cycle of a mounted tire, it must be centered laterally on the roller drive shaft so that a center plane extending perpendicularly through the tire rotational axis is parallel to and remains at a fixed distance from the vertical plate 24.

This centering is accomplished by a tire spreading device including pairs of inner and outer spacer rings 72 and 74 provided at a space apart locations on the shafts 48, as best shown in FIG. 4. The shafts 48 for supporting and rotating a tire are hollow and contain a linear type actuator 49 which controls the tire bead spreading device. An inner spacer ring 72 is fixed to each shaft and the outer spacer ring 74 is movable on the shaft. The outer ring is connected to an actuator piston 76 inside the shaft by a pin connector 78 which extends through a slot 80 in the shaft. Thus, the outer ring is movable by the actuator piston 76 whose outer end bears against a coiled spring 82 within the shaft which normally urges the outer ring 74 toward the inner ring 72.

When a tire is initially installed on the machine for testing, the spacer rings 72 and 74 are relatively close together and can readily fit between the tire beads. Once the tire is supported on the two shafts 48 the actuators 49 in each shaft 48 may be activated to push the movable rings 74 outwardly against the springs 82 and thereby spread the tire beads apart. Extra spacer rings 84 and 85 are provided on each shaft outwardly and inwardly from the spacers 72 and 74 to accommodate tires of different sizes merely by being moved adjacent the fixed and movable spacer rings before a tire is placed on the machine.

The coordinating mechanism 22 for controlling the movements of the transmitter transducer 14 and receiver transducer 16 during an inspection cycle is best shown in FIGS. 2 and 3 and also FIGS. 8A and 8B. This entire mechanism is supported by two pairs of upper and lower rigid shafts 86 and 88 which extend horizontally through spaced apart openings 90 in the vertical plate 24 for the enclosure 26.

Within the enclosure 26, on the inside of the vertical plate 24, as shown in FIG. 2, the ends of each pair of shafts 86 and 88 are fixed by mounting blocks 92 to the ends of a rigid beam 94 that extends horizontally, parallel to the plate 24. Centrally located on the bar member is a bracket 96 for retaining the end of a threaded screw shaft 98. This latter shaft is engaged in a bearing nut 100 fixed to a bracket support 102 attached to the plate 24. The end of the shaft 98 extending above the nut is fixed to a rotatable crank 104. Manipulation of the crank enables the up and down positioning of the entire coordinating mechanism 22 including the yoke assembly 18 on the outside of the plate 24.

Also within the enclosure 26 are a series of boxes 91 for electronic components, pneumatic controls 93, a marker fluid reservoir 95 and a fluid pump 97, all of which comprise components of the apparatus embodiment described herein.

On the outside of the vertical plate 24, each pair of shafts 86 and 88 are held together at their outer ends by a plate 89. Each upper shaft 86 extends through a pair of spaced apart linear ball bushings 106 and 108 which are fixed to a horizontal carriage plate 110. Each of these carriage plates is also connected at one end to a vertical end portion 112 of a U-shaped frame member 114 having an elongated rigid interconnecting arm 116 which is parallel to and spaced outwardly from the vertical wall 24. Thus, the carriage plates 110 with the attached frame member 114 are capable of translating horizontally on the shafts 86 as a unit.

Mounted on each carriage plate 110 is a stepper motor 118 whose output shaft is connected to a right angle gear reducer 122. The output shaft 123 of each gear reducer is fixed to one side arm 124 of the movable yoke 18 that serves to carry the receiving transducer unit 16 around the outside of a tire being tested as will be described below.

The movable yoke member 18 is a U-shaped component having its pair of parallel side arms 124 connected together at one of their ends by a transverse member 128 that supports the receiving transducer unit 16. The yoke is pivotable about an axis through the shafts 123 on the two gear reduction units 122 that are parallel to the transverse member 128. The receiver transducer supported thereby can be made to follow a generally partial elliptical path around the outside of a tire being inspected. The elliptical path of the yoke is made possible by a pair of control rods 130. Each control rod has an inner end 132 that is pivotally mounted to the blocks 92 on the support beam 94 (see FIG. 3A) and has a bend 134 near its outer end. As also shown in FIGS. 8A and 8B, the extreme outer end of each rod is pivotally attached to a pin 136 that extends through a slot 138 in the yoke side arm 124. The pin 136 is connected to a movable block 140 within the arm which in turn is connected to a screw actuator 142. The latter extends outside the end of each yoke side arm and has a circular head 144 with a crank arm 146. Thus, rotation of the actuator screws by their respective crank arms will cause movement of the blocks 140 within the yoke arms and this pivot point of the control rods and hence controls the shape of the elliptical movement path of the yoke during a tire testing cycle. The precise position of the blocks can be maintained by reference to a position on each block and a scale 139 that is provided on the outside of each yoke arm (See FIG. 8A.) The adjustment in the position of the block 140 within each yoke arm 124 will also adjust the arcuate path of the yoke as illustrated by the diagrammatic views in FIGS. 3A–3C.

In FIG. 3A, the yoke is shown in its horizontal position as the stepper motors 118 commence to rotate it via the output shafts 123. As this rotation starts, the control rods cause the carriage plates 110 to move outwardly on the upper shafts 86. Thus, movement of the carriage plates and the attached frame member 114 continues as the yoke rotates through an intermediate position (FIG. 3B) and then to its outermost position (FIG. 3C).

As shown in FIGS. 8A and 8B, the receiver transducer 16 is attached to the transverse member 128 of the yoke 18 near its mid-point between the yoke side arms. A pair of spaced apart posts 147 provide guide members which extend through a base portion of a mounting fixture 148 for the receiver transducer. This base portion is connected to the yoke member 128 by a pair of linear bearings 149 provided around each of the guide posts, thereby enabling the receiver unit 16 to move relative to the yoke member 128. The receiver transducer unit is also pivotally connected to a pair of arms 150 that extend from the base portion of the mounting fixture, and receiver transducer housing is provided with a pair of spaced apart cam followers 151. These followers fit within a pair of grooves or tracks 152 and 153 which are formed within a generally C-shaped cam plate 154 that is adapted to extend across and around the tread area of the tire being tested and at a substantially uniform distance therefrom. As shown in FIG. 4, the cam plate is connected by a hinge 155 to an upright support 156 attached to a base member 157 connected to the support members 54. When not in use, the cam plate 154 is rotated backwardly to permit the positioning of a tire to be tested, and once the tire is supported on the drive rollers 48 the cam plate can be rotated forwardly until its outer end surface 157 fits flush against a horizontal flange 158 on the end plate 52. A suitable latch on the flange 158 can then be moved to secure it in the closed position. For tires of substantially different size and/or configuration, a modified cam plate with different cam tracks can be easily installed to provide the precise positioning required for the receiver transducer.

As shown in FIG. 3, the transmitter transducer unit 14 is mounted on a support bracket 166 anchored on and extending upwardly from the interconnecting arm member 116 of the frame member 114, and it is positioned between the yoke end portions so that the axis of a rotatable mirror 15 for the transmitter transducer means is parallel to a rotational axis of yoke 18. The mirror 15 is spaced from a sonic generator 170, both being attached to a rigid platform member 172 supported by the bracket 166. The mirror 15 for the unit 14 is connected for rotation to a second stepper motor 174 which is electrically connected to and thus controlled by the main stepper motors 118. Thus, there is a fixed relationship between the rotation of the yoke assembly 18 and the mirror 15 of the transmitter transducer means 14.

The transmitter transducer unit 14 is also movable vertically from a lower stored position before a tire is installed on the apparatus to an upper position within the tire. Thus, the supporting bracket 166, as shown in FIGS. 4 and 8A is attached to a linear actuator 167 that is supported on a base member 169 fixed to the intermediate frame member 116.

The yoke stepper motors 118 operate at a rate, e.g. 18 steps per second at 1.8° rotation per step. The gear reducer 122, is selected to have a 30:1 reduction ratio so that its output shaft therefore rotates the yoke 18 at an angular rate of 1.1° per second. A programmable divider circuit (not shown) having a ratio less than than 30:1 and electronically connected to stepper motors 118 provides stepping pulses to the 1.8° per step transmitter stepper motor 174 which rotates the mirror 15 for the transmitter transducer. Thus, the mirror 15 rotates at a slightly greater angular rate than the yoke 18 and in synchronism with it. Therefore, the transmitter transducer angularly gains as the side walls are inspected to produce the FIG. 5 exit patterns. Since the transmitter mirror and the yoke must rotate at least a full 180° during one inspection cycle, the complete cycle may be accomplished in about 100 transmitter motor steps or 180 seconds. At each of the corners of the cam plate 154, the transmitter stepper motor is electronically temporarily inhibited by a non-reflective spot or flag 175 mounted on the cam plate 154 until the receiver transducer "leads" the transmitter mirror with the transmitter transducer. The net effect is that, as the yoke and receiver continuously rotate through their 180° arc, the transmitter mirror angle is automatically controlled to produce the FIG. 5 exit pattern required.

At the beginning of an inspection cycle, the yoke 18 is positioned to its maximum rotative position on one side of the tire. In this position the transmitter transducer 14 is at one extreme end of its translation position on the line of travel between the tire sidewall, and the mirror 15 of the transmitter transducer is in a horizontal position. Accordingly, the receiver transducer 16 on the yoke 18 is spaced directly outwardly from the nearest tire sidewall and is horizontally oriented to receive the collimated acoustic energy from the transducer transmitter through the tire. The positional relationship between the mirror of the transmitter transducer 14 and the receiver transducer 16 for a complete inspection cycle is shown diagrammatically in FIG. 5.

As the testing cycle commences, each 28 pulses, i.e., of the stepper motors 118, causes $28/30 \times 1.8° = 1.68°$ of rotation of the yoke 18 towards its other extreme 180° position and it also causes the inner stepper motor 174 to rotate the mirror 15 of the transmitter transducer $1.8° \times 28/28 \times 1.8°$. The action of the control rods 130 also causes the carriage plates 110 and then the U-frame 114 and the transmitter transducer to move along the translation line between tire sidewalls after a certain amount of rotation in the extreme end position. Since the yoke is travelling at a constant radius around the transmitter reflector and the receiver transducer is not, a linear potentiometer 400 connected between receiver carrier and the yoke applies a varying control voltage to a processor 196 (See FIG. 6) to adjust the processor delay according to the variation of the acoustic time of flight path between the transmitter and receiver.

OPERATION OF THE COORDINATING MEANS

In operation, once a tire has been set upon the drive shafts 48 and centered (by the spacers 72 and 74), there exists a horizontal plane in which the axis of rotation of yoke 18 and the mirror or reflector 168 of the transmitter transducer 14 must travel in order to properly inspect the tire. To establish the axis at the level of this plane, the horizontal shafts 86 of the coordinating assembly may be adjusted vertically by turning the hand wheel 104 which raises or lowers the beam member 94 to which the horizontal shafts are attached, as shown in FIG. 2. Once the optimum level of yoke axis has been set, the inspection process can commence.

In accordance with the invention, the inspection of a tire is accomplished by scanning its entire structure from sidewall to sidewall. As the tire is rotated, the transmitter transducer 14 is moved in incremental steps within the tire from one side to the other covering a sweep of around 180° while emitting time spaced bursts of collimated acoustic energy at about 80 bursts per second. Simultaneously, movement of the receiver transducer 16 outside the tire is controlled by the yoke 18 and cam plate tracks 152 and 153 to maintain substantial alignment with the transmitter transducer 14 and thus receive the energy transmitted through it. Accordingly, the combination of the tire's rotation, the step rotation along with lateral movement of the transmitter transducer within the tire and the frequency of the acoustic energy bursts, causes the tire to be completely covered from one sidewall to the other by a spiral pattern of overlapping circular areas 17 on the tire through which the collimated acoustic energy has been passed. For each circular area, the collimated energy is received by the receiver transducer 16 and evaluated immediately to determine if a structural flaw is present. If a flaw is detected, the marking device 20 is automatically activated to mark the flaw area on the tire.

The function of the various elements of the coordinating mechanism in maintaining the alignment of the transmitter transducer and receiver transducer is shown diagrammatically in FIGS. 3 and 4. In FIG. 4, a typical tire is shown in cross-section as it appears during an inspection cycle with the beads of the tire on the driver shafts 48 and held slightly apart by the spacers 72 and 74. The transmitter transducer mirror 15 is at the center of the tire and the receiver transducer 16 is retained on the contoured tracks of the cam plate 154 by its inner and outer follower wheels while outside the tire and directly above the transmitter mirror.

A series of relative intermediate positions of the transmitter and receiver transducer inside and outside the tire during a single inspection cycle is shown diagrammatically in FIG. 5. The transmitter transducer essentially moves along a straight line that extends through the opposite sidewalls of the tire and between end joints on the line. Since the collimated acoustic energy must be directed normal to the inside surface of the tire, the transmitter and receiver are translated laterally slightly with each rotational step as they are rotated through their inspection arcs. Translations of the transmitter transducer are relatively large for most of the width of the tire which comprises the tread area, because here the curvature of the inside tire surface is relatively slight. Thus, as shown diagrammatically in FIG. 5 when the transmitter mirror reaches the end points of its translation movement during a cycle it essentially ceases the translation movement along the transverse line and rotates only during each remaining step increment of the cycle, to cover the sidewall area of the tire, thereby continuing to cause each collimated acoustic pulse to impinge perpendicularly against the inside tire surface.

Defect Detection Circuit

The generation and processing of the electrical data produced by the apparatus 10 during each testing burst of collimated ultrasonic energy through a tire is provided by a circuit 190 which will be described with reference to FIG. 6.

This circuit comprises a transmitter section 192 for the transmitter transducer, a receiver transducer section 194, a processor 196, an inspection timing control section 198 and a display and control panel 200. As shown, a repetition rate generator 202 is preset to produce a pulse output rate sufficiently high to assure adequate inspection density. This pulse is furnished to a junction 204 from which it is supplied via a lead 206 to a pulse width generator 208 in transmitter section whose output enables an oscillator 210. The oscillator drives a power amplifier 212 with a sufficient number of cycles to allow a resonant transmitter transducer 214 to build up to maximum output and produce a burst of energy that is directed by the transducer mirror 168 to illuminate an area of the inner surface of the tire 12 being tested.

Now, in a receiver section 194, the receiver transducer 16 receives a small amount of the transmitted signal through the integral tire wall along with ambient noise. The resulting noise only or signal plus noise voltage from the receiver transducer is amplified by a preamplifier 214.

In the connected processor section 196 the output from the preamplifier is furnished through a capacitor 216 to a variable gain amplifier 218 and then through an A.C. coupled tuned filter 220 to a fixed gain direct coupled amplifier 222 to further amplify the signal plus noise in accordance with an automatic gain control AGC voltage applied via a feedback lead 224 to the variable gain amplifier 218. A precision detector 226 receives the amplified noise only (VN) or signal plus noise (VS+VN) voltage and applies a rectified voltage to an integrator 228. This integrator has an enable FET switch SW1 in parallel with a capacitor 230 whose closing member is connected through the timing control circuit 198 to the repetition rate generator 202. After an appropriate delay from the repetition rate generator caused by the delay generator 300, the enable SW1 is caused to open twice, permitting integration of (1) the ambient amplified noise voltage just prior to the signal arrival time; and (2) the amplified signal plus ambient noise voltage during the signal arrival time.

The integrator 228 has two output leads connected to one terminal of a FET switch SW2 and a FET switch SW3 respectively. The output terminals of these switches are interconnected by a lead 232 having a pair of capacitors C1 and C2 connected to ground. Field effect switches SW2 and SW3 along with capacitors C1 and C2 and appropriate high input impedance buffer amplifiers (not shown) comprise a dual channel hold circuit holding both the integrated VN voltage and the integrated VS+VN voltage. The output terminal for the switch SW2 is connected via a lead 236 to another terminal 238. The voltage (VN) at this terminal from SW2 represents the noise factor while the voltage (VS+VN) at a terminal 240 from SW3 is equivalent to signal plus noise. One pair of leads 242 and 244 are connected from terminals 238 and 240 to a subtractor circuit 246 whose output produces a voltage (VS) equivalent to signal only and is connected to a slow AGC amplifier 250 which provides the feedback AGC control signal. The resulting long time averaged voltage from amplifier 250 is almost solely due to the received and integrated VS only. The feedback AGC signal is connected to the normally closed Hold/Track AGC switch SW4 and in normal operation to a voltage follower 405. The feedback AGC voltage from voltage follower 405 is furnished to variable gain amp 218 via lead 224, and it also provides an output connected through a terminal 252 via a lead 254 to a "signal average" indicator 256 on the display panel 200.

Branching from the AGC output lead 224 to the variable gain amplifier 218 is a lead 257 connected to threshold potentiometer 406. The wiper of potentiometer 406 is connected via lead 259 to the inputs of comparators 262 and 260 and thus establishes a reference input voltage (VS Ref.) to comparators 262 and 260 which may be adjusted, via threshold potentiometer 406, to be any fraction of the average VS voltage.

With the VS Ref. voltage established at one input of comparator 260, and the integrated, sampled, and held VN voltage at the other input, comparator 260 will produce an output when VN exceeds VS Ref. whenever there is a long term of signal loss or excessive ambient noise. This output in turn opens gates 274 and 278 disallowing any output from gate 274 to a defect totalizer and from gate 278 to an inspection totalizer upon the arrival of the strobe pulse.

With VS Ref. established at one input of comparator 262 and integrated, sampled, and held VS+VN voltage at the other input, comparator 262 will produce an output when VS and VN does not exceed VS ref (when a defect is sensed), which is a fraction of the long term derived VS average.

The output of comparator 262, in turn, will close gate 274 (if no output was provided by comparator 260) and upon arrival of the strobe pulse gate 274 will output a pulse to increment the defect totalizer 286.

A lead 258 from the VN terminal 238 is furnished as one input to a first comparator 260 whose other input 261 is connected to a VS Ref. Similarly, a lead 263 from the (VS+VN) terminal 240 is furnished to a second comparator 262 which has another input 264 connected to a VS Ref. A second lead from (VS+VN) is furnished to real time sample indicator 265.

The output from comparator 262 is supplied to a gate 274. The output from comparator 260 is supplied through a terminal 276 to gate 274 and to a gate 278.

In the timing control circuit 198 the output from the repitition rate generator 202 is furnished via a lead 298 to an adjustable delay generator 300 which is controlled by a potentiometer 400 to provide a time delay corresponding to the varying time of flight of the ultrasonic signal from the transmitter transducer 14 to the receiver transducer 16. Linear potentiometer 400 is connected between the fixed radius yoke 18 and the receiver so as to produce a voltage change proportional to the transmitter/receiver distance change as the receiver transverses the cam plate 25. The output from delay generator 300 is supplied to a differentiator 302 whose output is connected through a terminal 304 to an "OR" gate 306.

The output of "OR" gate 306 i connected to a terminal 308 from which extends a lead 310 connected to the "S" input of an R-S flip-flop 312 whose output is connected to operate SW1 of the integrator 228. Another lead 314 from the output terminal of "OR" gate 306 is connected to a pulse width generator 316. The output of the pulse width generator is furnished to a differentiator 318 whose output is supplied to a sample generator 320. The output from the sample generator is supplied through a terminal 322 to a differentiator 324 and through another terminal 326 to a recycle delay 328. A lead 330 from the terminal 322 is connected to a pair of gates 332 and 334. A lead 336 from the output terminal 326 of the differentiator 324 is connected to the "R" input for the flip-flop 312.

A lead 338 from the output terminal 304 for the differentiator 302 is supplied to the "S" input of an RS flip-flop 340 to put it in its set state. The "R" input to this flip-flop is provided via a lead 342 through a differentiator 344 whose input is provided from the recycle delay 328. One output from the flip-flop 340 is furnished to the gate 334 and another output is furnished to the gate 332 as well as through a differentiator 341 to the "OR" gate 306. The operation of the defect detection circuit 190 may be summarized as follows with reference to FIG. 6 and the timing diagram of FIG. 7. When a single pulse is provided by the repetition rate generator 202 to the terminal 204 it travels to the transmitter circuit so that the transmitter transducer 14 is activated as previously described to produce a burst of ultrasonic energy directed normally to the inside surface of the tire. The repetition rate generator pulse is also provided to the timing control section 198 to trigger the delay generator 300. This produces a pulse of a predetermined length (which is proportional to the distance between transmitter and receiver transducers 14 and 16 and thus the time of flight of the ultrasonic pulse between them). The trailing edge of the pulse from the delay generator is differentiated by element 302 to produce a pulse which: (1) sets the R.S. flip-flop 340 and (2) passes through the "OR" gate 306 to set the R.S. flip-flop 312. When R.S. flip-flop 312 is set, it opens SW1 and enables the integrator 228 so that it will commence integrating.

The output from "OR" gate 306 supplied to R.S. flip-flop 312 is simultaneously supplied to pulse width generator 316 which produces a timing pulse of a predetermined length whose trailing edge is differentiated by element 318 and supplied to the sample generator 320. The output from this sample generator is furnished to gate 334 which provides a signal that closes SW2 and causes the integrator 228 to supply the integrated voltage (VN) equivalent to noise only to capacitor C1. The output from the sample generator is also differentiated by element 324 whose output is supplied via lead 336 to R.S. flip-flop 312 causing it to disable the integrator. Thus, at this point the capacitor C1 holds a voltage value for ambient noise. Now, the output from differentiator 324 is also furnished to the recycle delay element 328 which provides a predetermined time space between first and second integrations during a single cycle. The output from the recycle delay 328 is differentiated by element 344 and is supplied to the R.S. flip-flop 340 causing it to reset and provide an output that (1) activates gate 332 which in turn closes SW3 on the integrator 228 causing a second integration for signal plus noise (VS+VN) to commence; and (2) simultaneously provides a differentiated signal through "OR" gate 306 to the R.S. flip-flop 312 to again open SW1 and enable the integration. Thus, in this second integration a voltage value for signal plus noise is stored and held in capacitor C2. At the trailing end of the second sample generator pulse, the differentiator 324 again produces a signal which terminates the second integration.

During each inspection cycle the noise only integration voltage at terminal 238 and the signal plus noise integration voltage at terminal 240 are supplied to the subtractor circuit 246 which may be a conventional operational amplifier. The output of the subtractor is supplied as one input to the slow AGC amplifier 250 which functions to filter out any rapid cycle changes and provides an output signal that is substantially amplitude constant but which changes slowly in response to signal variations. The output from this AGC amplifier is furnished via the hold/track circuit: (1) to the indicator 256 on the display panel which provides a visual means for observing signal variations during an inspection cycle; as a feedback signal to the variable gain amplifier 218 via lead 224 to maintain stability with the received test signal; and (2) as an input to the threshold potentiometer 406.

If there is excessive ambient noise around the apparatus during a test cycle, a voltage from the noise only integration terminal will be supplied via lead 258 to comparator 260. This comparator has a signal level reference voltage which is a fraction, e.g. 80% of the VS average voltage and will produce an output if the integrated noise voltage exceeds the reference voltage. The output of comparator 260 disables gates 274 and 278 to turn off the apparatus if excess noise is present which would negate the effectiveness of an inspection cycle.

Now, assuming that excess ambient noise is not present and integrated signal only voltage (VS) is producing a stable AGC amplifier, the signal plus noise (VS+VN) is supplied to comparator 262. Here, the ref. voltage is maintained at a value which is preset to a level which is a fraction, e.g. 80% of the average signal. If, during one of the ultrasonic pulses in an inspection cycle, a defect, such as a delamination in the tire structure, is encountered the integrated VS+VN signal will fall producing an output from the comparator 262 and thereby indicating the tire defect. This comparator output is supplied to gate 274 which (1) furnishes a signal to the display panel 200 that activates the defects counter 286 and the indicator lamp 287; and (2) furnishes a signal via lead 288 to the spray delay 290. This calibrated delay allows the rotation of the tire to carry the detected defect from the proximity of the receiver 16 to the proximity of the spray marker 20. The delayed signal then activates the spray marker, causing a marking substance to be sprayed onto the tire in the near vicinity of the defect. This delay is also adjusted so that the spray marker does not interfere with the periodic ultrasonic signal burst.

To facilitate automatic control of the machine 10 and recordal for inspection results during inspection cycles, the combined control and display unit 275 is attached to an overhead arm 277 that is pivotally attached to the enclosure 26. As shown in FIG. 9, the front console for the unit provides a power on switch 412, a forward-reverse selector 414, a fast-slow selector 416 and the hold-track control 248 in addition to the manual-auto switch button 402, and switch buttons for home-abort 420, scan-load 422 and defect-test 423. Indicators are also provided for showing the number of tires inspected 424, the number of pulsed inspections for one inspection cycle 292 and the number of defects detected during the cycle 286. Other recorded instruments well known in the art could be connected to the display unit to provide readable printouts of test results where desired.

MANUAL AND AUTOMATIC SCAN CONTROLS

In FIG. 10, a block diagram is provided to illustrate the electro-mechanical controls required to produce either a manual or an automatic scan of a tire. FIG. 10 may be more readily understood by reference to FIG. 5, which indicates the relative required angles and positions of the transmitter mirror or reflector 15 and the receiver transducer 16 for a particular tire shape.

After a tire has been loaded onto the roller shafts 48 and the cam plate 154 has been closed, a scan switch 422, as shown on the control panel (FIG. 9), may be actuated. This causes the apparatus control logic 404 to: (1) actuate the tire bead spreader mechanism 49 (FIG. 4); (2) start the tire rotation motor 62; (3) start a stepper motor clock oscillator 406; (4) start a transmitter stepper motor driver 408 and yoke stepper motor drivers 410 to drive them in a forward or clockwise motion; and (5) enable the signal processor 196. (See FIG. 10.)

At each clock pulse from the clock oscillator, the yoke stepper motor drive 410 causes the yoke stepper motors 118 to advance 1.8°. In the embodiment shown and described, the 30:1 gear reducers 122 in turn reduce the actual yoke angular change to 0.06° per clock oscillator pulse. Since the clock oscillator is operating at about 18 pulses per second, the yoke will traverse its 180° arc in about 2.8 minutes. In actual operation, the yoke may be allowed to travel somewhat beyond the horizontal centerline of the tire for a total travel of 200°, yielding a total inspection time of three minutes. Incremental angles of the yoke as it traverses its arcuate travel are shown in FIG. 5 by the exit arrows. As indicated, at one position of incremental yoke angle (A) up the tire sidewall, the required incremental transmitter reflector 15 angle (B) must be greater when the yoke arrives at the position indicated in order for the emergent collimated sound beam to be interrupted by the receiver transducer 16, due to the refractive characteristics of the tire. As shown in FIG. 5, the required angular relationship between the transmitting mirror 15 and the yoke 18 as the tire is transversed must take into account the fact that: (1) the yoke and transmitter mirrors angles must be aligned when intercepting the horizontal cross section axis of the tire; (2) the transmitter mirror angle (B) must progressively increase faster than yoke angle (A) as the sidewall is scanned; (3) the transmitter mirror angle (B) must suddenly be caused to be less than yoke angle (A) after the corner on the cam plate is turned; (4) the transmitter mirror angle (B) must equal yoke angle (A) at the tread center line and increase faster than yoke angle (A) from the tread centerline to a corner; and (5) after each corner turn, the transmitter mirror angle (B) must suddenly be caused to be less than the yoke angle (A) and then must progressively increase faster than yoke angle (A) until the horizontal cross section axis of the tire is reached. The required angular relationship between transmitter mirror 15 and yoke assembly 18 is accomplished with the use of a programmable divider 173, a system of flags 175, a flag sensor 177, a gate 179, the transmitter stepper motor driver 408 and the transmitter stepper motor 174.

The field programmable divider 173, typically set to divide the stepper motor clock oscillator output by 28:1, produces an effective rotation of the 1.8° per step transmitter stepper motor 174 of 1.8 divided by 28 which equals 0.064 degrees per clock oscillator 406 output pulse.

Therefore, the transmitter mirror 15 angle (B) gains approximately 0.064 minus 0.060 or 0.004 degrees over the yoke assembly angle and upon each clock oscillator output pulse and produces the required leading transmitter mirror angle (B) shown in FIG. 5. Near each tire corner, where the receiver is rapidly rotated by its complete tracks 152 and 153, a flag 175, mounted on cam plate 154 (see FIG. 3), is sensed by a flag sensor 177. The flag sensor 177, which is mounted on the receiver housing, is of the retro-reflective type which produces a light beam directed at the cam plate. When the beam strikes a flag 175, the sensor 177 produces an output signal. The flag sensor output is furnished to a gate 179 which controls the transmitter stepper motor. Thus, the flag functions to temporarily inhibit the transmitter stepper motor 174 while the yoke assembly 18 continues to rotate during a test cycle, until the yoke angle (A) exceeds the transmitter mirror 15 angle (B) by the required amount. When the end of the flag 75 is reached, the transmitter stepper motor 174 is again enabled so that its movement is properly coordinated with the receiver.

Therefore, it can be seen that with the proper programmable divider 181 ratio and the proper flag 175 lengths, the desired angular relationships between the transmitter mirror 15 and the yoke assembly 18 can be maintained.

When the scan (visualized left to right in FIG. 5) has been completed after the clockwise traverse, a clockwise limit switch 183 is encountered by the yoke. The control logic 404, in turn, reverses stepper motor directions and accelerates the stepper motor clock oscillator 406 to produce a rapid return of the yoke assembly and transmitter until a counterclockwise limit switch 185 is encountered, where the control logic stops the tire rotation and retracts the transmitter to permit unloading the tire.

From the foregoing it is seen that the present invention provides an efficient and highly effective tire inspection system which measures the structural integrity of the tire by covering it with a multiplicity of overlapping areas of concentrated, collimated ultrasonic energy and then analyzing each area electronically. The defect analysis circuitry for the system minimizes the influence of ambient noise and maintains a reliable, repetitive mode of operation for producing signal information that indicates the presence and precise location of internal tire defects.

To those skilled in the art to which this invention relates, many changes in construction and widely differing embodiments and applications of the invention will suggest themselves without departing from the spirit and scope of the invention. The disclosures and the descriptions herein are purely illustrative and are not intended to be in any sense limiting.

What is claimed is:

1. An apparatus for inspecting both tread and sidewall areas of a tire for structural defects comprising:
   an upright housing;
   means extending from said housing for supporting and rotating a tire at a constant rate during an inspection cycle;
   a movable transmitter transducer means for directing a plurality of successive collimated bursts of ultrasonic energy against the surface and through the tire, said bursts passing through the tire and forming inspection areas having the same diameter and overlapping each other as the tire is rotated during an inspection cycle;
   a receiver transducer means independently movable for receiving and collimated ultrasonic energy that passes through each inspection area;
   coordination means for controlling the movements of said transmitter transducer means and said receiver transducer means from one sidewall of the tire to the other sidewall generally parallel to its axis of rotation so that successive bursts are directed through the tire as it rotates while maintaining substantially the same distance between said receiver transducer means and the tire surface;
   electrical means for evaluating the strength of the energy received by said receiver transducer means for each burst; and
   means responsive to the evaluation by said electrical means for providing a visual indication of a structural defect in the tire being inspected wherever a said burst of energy is directed at said defect.

2. An apparatus for inspecting both tread and sidewall areas of a tire for structural defects comprising:
   an upright housing
   means extending from said housing for supporting and rotating a tire about its axis at a constant rate during an inspection cycle;
   transmitter transducer means for directing a plurality of successive collimated bursts of ultrasonic energy against the inside surface of the tire, each said collimated burst passing through the tire in an inspection area of the same diameter;

means for moving said transmitter transducer means within the tire generally parallel to the tire axis as the tire is rotated so that said inspection areas overlap and cover the total inspection area of the tire structure to be inspected;

receiver transducer means for receiving the collimated ultrasonic energy that passes through the inspection area on the tire with each burst;

coordination means for moving said receiver transducer means from one sidewall of the tire to the other sidewall so that it is always positioned outside the tire to receive the energy passing through the tire with each burst and including means for moving the receiver transducer means independently from said transmitter transducer means while maintaining it at substantially the same distance from the outside tire surface;

electrical means for evaluating the energy received by said receiver means for each burst to determine if a defect is present in the inspection area for that particular burst.

3. The apparatus of claim 2 wherein said means for supporting and rotating a tire comprises a pair of rotatable shafts on said housing supported by and extending horizontally from said upright housing, said shafts being adapted to extend through the tire and engage the tire beads; and drive means for rotating said shafts at a predetermined constant rate to thereby rotate the tire about an axis perpendicular to said upright plate.

4. The apparatus as described in claim 3 including a pair of spaced apart spreader means on each said rotatable shaft, said spreader means being adapted to bear against the tire beads, and actuator means for moving one said spreader means relative to the other spreader means on each said rotatable shaft to retain the tire in a preselected position before an inspection cycle is initiated.

5. The apparatus as described in claim 2 wherein said transmitter transducer means comprises an ultrasonic generator spaced from a rotatable 90° sonic deflector and said receiver transducer means comprises a rotatable ultrasonic receiver spaced from said transmitter transducer.

6. The apparatus as described in claim 2 wherein said coordination means comprises:

a pair of spaced apart supports extending horizontally from said housing;

a carriage plate movably mounted on each said support;

a pair of first stepper motors each connected to a gear box with an output shaft on each said carriage plate;

frame means having an intermediate cross member with end portions fixed to said carriage plates;

means for mounting said transmitter transducer means on said frame means;

a second stepper motor connected to said transmitter transducer means and electrically connected to said first stepper motors;

yoke means between said supports having spaced apart parallel end portions and an interconnecting span member, each said end portion being connected to a said gear box shaft to thereby cause said yoke means to rotate;

a pair of control rods, each rod pivotally connected at its inner end to said housing and at its outer end to a yoke end portion at a preselected distance from a said gear box shaft;

a receiver transducer means pivotally mounted on said interconnecting span member of said yoke means and having cam follower means attached thereto;

a fixed cam plate located between and extending generally parallel to said supports and thereby adapted to extend transverse to and around the tread area of a tire being inspected, said cam plate having cam track means to receive said follower means on said receiver transducer means;

whereby rotation of said yoke means by said first stepper motors causes said control rods to move said carriage plates on said supports and also to move the attached frame means relative to said housing, said frame means thereby moving said transmitter transducer means horizontally while said yoke means moves said receiver means in a generally elliptical path along said track means of said cam plate so as to be constantly positioned to receive collimated bursts of energy that pass through the tire from said transmitter transducer means.

7. The apparatus as described in claim 6 including means on said yoke means for adjusting the location of the outer end connections for said control rods on said yoke end portions to thereby change the amount of horizontal travel for said yoke means during its rotation.

8. The apparatus as described in claim 7 wherein said follower means on said receiver transducer comprises a pair of spaced apart rollers, and said cam track means comprises a pair of spaced apart grooves on said cam plate for guiding said rollers.

9. The apparatus as described in claim 7 wherein said cam plate generally has an inverted U-shape and extends downwardly along opposite sidewalls of a tire being inspected.

10. The apparatus as described in claim 9 including a mounting means attached to said housing for supporting said cam plate; having means at one end of said cam plate for connecting it to said mounting means and latch means at its other end for securing it over a tire in its operating position.

11. The apparatus as described in claim 6 wherein said means for mounting said transmitter transducer means on said frame means includes an actuator means for moving said transmitter transducer means from a retracted position vertically to an operative level after a tire has been installed on said apparatus for inspection.

12. An apparatus for inspecting both tread and sidewall areas of a tire for structural defects comprising:

transmitter transducer means including a movable 90° deflector within the tire for producing collimated bursts of ultrasonic energy having limited cross sectional area;

receiver transducer means outside the tire;

means for moving said transmitter transducer means along a straight line extending between the tire sidewalls as it emits successive time spaced bursts of energy;

means for rotating said transmitter transducer deflector through an angle as it is moved along said straight line so that ultrasonic energy of each burst impinges at a right angle against the inside tire surface;

coordination mans for moving said receiver transducer means outside said tire from one sidewall across its tread area to the other sidewall while maintaining its alignment with said transmitter transducer means and a substantially constant distance from the outside tire surface;

means for also rotating said receiver transducer means so as to maintain alignment with said transmitter deflector during each energy burst;

means for measuring the ultrasonic energy passing through the tire and received by said receiver transducer means for each burst; and means for evaluating the energy measurement made by said receiver transducer during each burst to determine the presence of a defect in that particular burst.

13. The apparatus as described in claim 12 wherein said means for evaluating the energy received by said receiver transducer means comprises an electrical circuit including:

means for determining an electrical value for ambient noise only;

processor means for determining an electrical value for ambient noise plus the signal for energy received by said receiver transducer;

means for comparing the electrical value of noise plus signal with a preset value and for producing an output signal denoting a tire defect when the noise plus signal value falls below the preset value.

14. The apparatus as described in claim 13 wherein said processor means includes an integration means with capacitor means for temporarily storing two outputs; and timing control circuitry for causing said integration during each burst cycle to integrate a first time to store an output representative of ambient noise only and thereafter to integrate a second time to store an output representative of noise plus signal.

15. The apparatus as described in claim 13 including means for comparing said electrical ambient noise value with a preset fraction of average signal level for each said burst; and means responsive to an excess noise level for aborting the evaluation of data for the bursts during which excess noise is present.

16. The apparatus as described in claim 13 including means for deriving an electrical value of an AGC voltage from signal-only energy received during each burst.

17. The apparatus as described in claim 12 including a marking means associated with said receiver transducer means for marking the outside of a tire within the area of a particular burst of energy in response to a signal from said comparing means indicating that a defect is present in that particular burst area.

18. The apparatus as described in claim 17 wherein said marking device comprises a pressure producing nozzle for a marking fluid aligned with said receiver deflector.

19. The apparatus as described in claim 12 including a display panel which indicates the total number of bursts during an inspection cycle, the total number of defects, and an indicator light which is activated for each defect detected.

20. The apparatus as described in claim 19 wherein said display panel also provides an indicator of the AGC signal average during successive bursts of an inspection cycle.

21. A method for inspecting both tread and sidewall areas of a tire for latent structural defects comprising the steps of:

rotating the tire about its axis at a constant rate;

directing a plurality of individual time spaced bursts of collimated ultrasonic energy through the tire wall as it is rotating, each said burst covering a limited area of energy exposure on the tire, said areas overlapping but having spaced apart centers on the surface of the tire being inspected, said overlapping burst areas covering said tire surface from sidewall to sidewall;

receiving for each separate burst the collimated ultrasonic energy which is transmitted through the tire;

evaluating the received energy for each burst; and comparing the electrical equivalent of actual received energy with a derived average value thereof to provide an output signal when a tire defect is present within the limited area of each burst.

22. The method as described in claim 21 including the further steps of marking the tire within the limited area of every burst for which a defect is detected.

23. The method as described in claim 21 wherein said plurality of bursts of ultrasonic energy is directed from transmitter transducer means within the tire that moves between each burst so that the ultrasonic energy for each burst is directed substantially perpendicular to the inside surface of the tire.

24. The method as described in claim 21 wherein the ultrasonic energy for each collimated burst which passes through the tire is refracted from its outer surface and is intercepted by a moveable receiver transducer means which remains at substantially the same distance from the outside tire surface for each burst.

25. The method as described in claim 21 wherein said transmitter transducer means is moved transversely as well as rotated on successive bursts during an inspection cycle.

26. The method as described in claim 21 including the step of moving said receiver transducer means in a predetermined arcuate path while also rotating it so that it is constantly positioned to receive the collimated ultrasonic energy passing through said tire with each burst.

27. The method as described in claim 21 including the steps of moving said transmitter transducer means inside the tire from one side of he tire towards the other side as it produces successive bursts, and simultaneously rotating the tire so that as the tire is being inspected it is covered by a spiral pattern of overlapping burst areas on the tire surface.

28. The method as described in claim 21 including the steps of transmitting the ultrasonic energy bursts through the tire by reflective means located inside the tire, and moving the receiver means outside the tire so that it is always positioned to receive each collimated burst of energy passing through the tire.

29. The method as described in claim 21 including the steps of:

providing a movable transmitter transducer means within the tire for directing said bursts of energy, and providing a moveable receiver transducer means outside the tire for receiving the energy of each burst that passes through the tire;

causing said transmitter transducer means to translate across the width of the tire and also rotate in increments for each burst, and causing said receiver transducer means to move arcuately and also rotate in increments for each burst so as to maintain alignment with the collimated energy which passes through the tire with each burst.

30. The method as described in claim 21 wherein the evaluation of the received energy for each burst comprises the steps of:
- obtaining an electrical value for ambient noise;
- obtaining an electrical value for noise plus a signal that is the electrical equivalent of received burst energy;
- comparing the noise plus signal value with a predetermined fraction of the normal level for a structurally sound tire;
- providing a visual indication of a tire defect if the aforesaid comparison of noise plus signal differs from the preset fraction of the normal level.

31. The method as described in claim 30 including the step of automatically aborting an inspection cycle if the ambient noise level exceeds a preset fraction of the normal level.

32. The method as described in claim 30 including the step of utilizing an AGC feedback signal to maintain a slow changing signal level;
- comparing the signal level for each burst with a preset fraction of the normal level; and
- automatically aborting the evaluation of data for those bursts of an inspection cycle which exceed the preset fraction of the normal level.

33. An apparatus for inspecting both tread and sidewall areas of a tire for structural defects while it is supported for rotation, comprising:
- movable transmitter transducer means inside the tire;
- means for moving the transmitter transducer means so that direct successive overlapping bursts of collimated energy are passed through the tire from one sidewall of the tire to the other, each said burst being directed at substantially a right angle to the inside surface of the tire;
- a receiver transducer means which is independently movable with respect to said transmitter transducer means and located outside the tire;
- means for moving said receiver transducer means so that it is constantly positioned to receive the maximum level of each burst that is emitted from said transmitter transducer means which passes through and leaves the outer surface of the tire;
- means for evaluating the energy received for each burst by said receiver transducer means to determine whether a tire defect exists therein; and
- means responsive to said evaluation means for indicating a defect for a particular burst when such defect is present.

34. In an apparatus for inspecting both tread and sidewall areas of a tire for structural defects while it is supported for rotation comprising a vertical support plate fixed to a housing:
- a movable ultrasonic transmitter transducer means adapted to be located inside the tire being inspected;
- an ultrasonic receiver transducer means which is movable independently from said transmitter transducer means located outside the tire;
- a means for supporting said transmitter and receiver means and for coordinating their movements relative to each other during a tire inspection cycle;
- spaced apart shafts extending horizontally from said support plate for supporting said coordinating means;
- a pair of spaced apart carriage means slidable on each said shaft;
- an interconnecting arm extending between said carriage means and parallel to said support plate;
- a first stepper motor and a connected gear reducer on each said carriage means, and shaft means extending from said gear reducers;
- a second stepper motor connected to said transmitter transducer means and electrically connected to said first stepper motors;
- yoke means between said supports having spaced apart parallel end portions and an interconnecting span member, each said end portion being connected to a said gear box shaft to thereby cause said yoke means to rotate;
- a pair of control rods, each rod pivotally connected at an inner end to said housing and at its outer end to a yoke end portion at a preselected distance from a said gear box shaft;
- said receiver transducer means being pivotally mounted on said interconnecting span member of said yoke means and having cam follower means attached thereto;
- a fixed cam plate located between and extending generally parallel to said supports, and thereby adapted to extend transverse to and around the tread area of a tire being inspected, said cam plate having cam track means to receive said follower means on said receiver transducer means;
- whereby rotation of said yoke means by said first stepper motors causes said control rods to move said carriers on said supports and also the attached frame means to move relative to said housing, said frame mans moving said transmitter transducer means horizontally and said yoke means moving said receiver in a generally arcuate path along said track means of said cam plate so as to be constantly positioned to receive collimated bursts of energy that pass through the tire from said transmitter transducer means.

35. An apparatus for inspecting a tire for structural defects comprising:
- means for supporting and rotating a tire at a predetermined constant speed during an inspection cycle;
- a first movable transducer means for transmitting collimated bursts of ultrasonic energy from inside the tire through the tire and second transducer means which is independently movable from said first transducer means for receiving the residual energy of each burst on the other side of the tire, each said burst forming an inspection area of uniform size;
- means for moving both said transducer means in increments for successive bursts generally parallel to the tire axis of rotation s that said bursts form a spiral pattern of overlapping inspection areas on the tire surface;
- coordination means for controlling said transmitting and receiving transducer means to that they are substantially aligned during each collimated burst to receive the energy transmitted through the tire from one transducer to the other;
- means for electrically evaluating the energy received for each burst; and
- means responsive to said evaluation means for providing a visual indication of a tire defect for a particular burst when such a defect is present.

36. The apparatus as described in claim 35 wherein said means for moving said transducer means comprises a first stepper motor means for rotating said transmitting transducer means, a second stepper motor means for moving said receiving transducer means around the outside of the tire and for moving said transmitting transducer means laterally within the tire as it is rotated.

37. The apparatus as described in claim 36 wherein said coordination mans includes a yoke means driven by said second stepper motor means, a generally inverted U-shaped cam plate with cam tracks extending partially around the tire on a line parallel with the tire's axis of rotation, said receiver transducer means being attached to said yoke means and having followers engaged in said cam tracks so as to follow a preselected path as said yoke means is rotated, and means for driving said first and second stepper motor means in unison.

38. The apparatus as described in claim 37 wherein said coordination means further includes means inhibiting said first stepper motor means when said receiver transducer means reaches preselected locations on said cam plate so that the relative transducers will be maintained to enable the receiving transducer to receive a high level of acoustic energy which passes through the tire.

39. The apparatus as described in claim 38 wherein said inhibiting means comprises flag members on said cam plate at spaced apart locations and sensor means responsive to said flag members connected to said movable receiving transducer and providing output means connected to said transmitting transducer means.

40. The apparatus as described in claim 37 including limit switches for controlling the travel of said yoke means through an arc of at least 180° for each tire inspection cycle.

* * * * *